United States Patent
Genta et al.

(10) Patent No.: US 9,868,932 B2
(45) Date of Patent: *Jan. 16, 2018

(54) BIOMASS HYDROTHERMAL DECOMPOSITION APPARATUS, TEMPERATURE CONTROL METHOD THEREOF, AND ORGANIC RAW MATERIAL PRODUCTION SYSTEM USING BIOMASS MATERIAL

(75) Inventors: Minoru Genta, Tokyo (JP); Ryosuke Uehara, Tokyo (JP); Hideo Suzuki, Tokyo (JP); Seiichi Terakura, Tokyo (JP)

(73) Assignee: MITSUBISHI HITACHI POWER SYSTEMS ENVIRONMENTAL SOLUTIONS, LTD, Yokohama-shi, Kanagawa (JP)

(*) Notice: Subject to any disclaimer, the term of this patent is extended or adjusted under 35 U.S.C. 154(b) by 515 days.

This patent is subject to a terminal disclaimer.

(21) Appl. No.: 13/132,034

(22) PCT Filed: Mar. 10, 2010

(86) PCT No.: PCT/JP2010/054022
§ 371 (c)(1),
(2), (4) Date: May 31, 2011

(87) PCT Pub. No.: WO2011/111189
PCT Pub. Date: Sep. 15, 2011

(65) Prior Publication Data
US 2011/0300617 A1 Dec. 8, 2011

(51) Int. Cl.
*C12M 1/38* (2006.01)
*C12N 1/22* (2006.01)
(Continued)

(52) U.S. Cl.
CPC .................. *C12N 1/22* (2013.01); *C12P 7/10* (2013.01); *C12P 19/02* (2013.01); *Y02E 50/16* (2013.01)

(58) Field of Classification Search
CPC ... C12N 1/22; C12P 19/02; C12P 7/10; Y02E 50/16; C12M 21/12
(Continued)

(56) References Cited

U.S. PATENT DOCUMENTS 3,985,725 A    10/1976   Lin
3,985,728 A    10/1976   Lin
(Continued)

FOREIGN PATENT DOCUMENTS

CA    2660990 A1    8/2009
CA    2666152 A1    4/2010
(Continued)

OTHER PUBLICATIONS

Arroyo-Lopez, F.N. et al., "Effects of temperature, pH and sugar concentration on the growth parameters of *Saccharomyces cerevisiae*, S. kudriavzevii and their interspecific hybrid", International Journal of Food Microbiology, vol. 131, pp. 120-127 (2009).
(Continued)

*Primary Examiner* — William H Beisner
*Assistant Examiner* — Danielle Henkel
(74) *Attorney, Agent, or Firm* — Westerman, Hattori, Daniels & Adrian, LLP

(57) ABSTRACT

A biomass hydrothermal decomposition apparatus that feeds a solid biomass material 11 from one side of an apparatus body 42, feeds pressurized hot water 15 from the other side, to hydrothermally decompose the biomass material 11 while bringing the biomass material 11 into counter contact with the pressurized hot water 15, dissolves hot-water soluble fractions in hot water, discharges the pressurized hot water
(Continued)

to outside from the one side of the apparatus body 42 as a hot-water effluent 16, and discharges a biomass solid 17 to the outside from the other side. The biomass hydrothermal decomposition apparatus includes: an internal-temperature cooling unit that rapidly drops a temperature after performing hydrothermal decomposition for a certain period of time; temperature measuring units $T_1$ to $T_8$ that measure an internal temperature; and a controller 100 that controls an internal temperature to be maintained at a predetermined cooling temperature by the internal-temperature cooling unit based on temperature measurement results obtained by the temperature measuring units $T_1$ to $T_8$.

7 Claims, 14 Drawing Sheets

(51) Int. Cl.
  *C12P 7/10* (2006.01)
  *C12P 19/02* (2006.01)

(58) Field of Classification Search
  USPC .................................................. 435/286.1
  See application file for complete search history.

(56) References Cited

U.S. PATENT DOCUMENTS

| | | | |
|---|---|---|---|
| 4,023,982 A | 5/1977 | Knauth | |
| 4,152,197 A | 5/1979 | Lindahl et al. | |
| 4,650,689 A | 3/1987 | Hedrick | |
| 4,746,401 A | 5/1988 | Roberts et al. | |
| 4,859,322 A | 8/1989 | Huber | |
| 5,348,871 A | 9/1994 | Scott et al. | |
| 5,411,594 A | 5/1995 | Brelsford | |
| 5,424,417 A | 6/1995 | Torget et al. | |
| 5,466,108 A | 11/1995 | Piroska | |
| 6,022,419 A | 2/2000 | Torget et al. | |
| 6,419,788 B1* | 7/2002 | Wingerson | D21C 1/02 127/37 |
| 8,123,864 B2 | 2/2012 | Christensen et al. | |
| 8,163,517 B2 | 4/2012 | Genta et al. | |
| 8,728,770 B2 | 5/2014 | Ishikawa et al. | |
| 9,102,956 B2* | 8/2015 | Genta | C10L 1/02 |
| 2007/0231869 A1 | 10/2007 | Holmgren et al. | |
| 2007/0259412 A1* | 11/2007 | Belanger et al. | 435/161 |
| 2008/0026431 A1 | 1/2008 | Saito et al. | |
| 2008/0032344 A1* | 2/2008 | Fallavollita | 435/72 |
| 2008/0044891 A1 | 2/2008 | Kinley et al. | |
| 2008/0299628 A1 | 12/2008 | Hallberg et al. | |
| 2010/0108567 A1 | 5/2010 | Medoff | |
| 2010/0184176 A1 | 7/2010 | Ishida et al. | |
| 2010/0269990 A1 | 10/2010 | Dottori et al. | |
| 2010/0285574 A1 | 11/2010 | Genta et al. | |
| 2010/0317843 A1 | 12/2010 | Sudhakaran et al. | |
| 2010/0330638 A1 | 12/2010 | Aita et al. | |
| 2011/0003348 A1 | 1/2011 | Genta et al. | |
| 2011/0079219 A1* | 4/2011 | McDonald | C13K 1/02 127/1 |
| 2011/0314726 A1 | 12/2011 | Jameel et al. | |
| 2012/0006320 A1 | 1/2012 | Nguyen | |
| 2012/0315683 A1 | 12/2012 | Mosier et al. | |
| 2014/0004571 A1 | 1/2014 | Garrett et al. | |
| 2014/0273127 A1 | 9/2014 | Fuchs et al. | |

FOREIGN PATENT DOCUMENTS

| | | |
|---|---|---|
| CA | 2750754 A1 | 1/2012 |
| CA | 2654306 C | 10/2013 |
| EP | 0 098 490 A2 | 1/1984 |
| JP | 9-507386 A | 7/1997 |
| JP | 11-506934 A | 6/1999 |
| JP | 2001-170601 A | 6/2001 |
| JP | 2002-059118 A | 2/2002 |
| JP | 2003-311141 A | 11/2003 |
| JP | 2004-105855 A | 4/2004 |
| JP | 2005-27541 A | 2/2005 |
| JP | 2005-168335 A | 6/2005 |
| JP | 2005-205252 A | 8/2005 |
| JP | 2005-229821 A | 9/2005 |
| JP | 2006-036977 A | 2/2006 |
| JP | 2006-068399 A | 3/2006 |
| JP | 2006-136263 A | 6/2006 |
| JP | 2006-223152 A | 8/2006 |
| JP | 2006-289164 A | 10/2006 |
| JP | 2007-112880 A | 5/2007 |
| JP | 2007-202560 A | 8/2007 |
| JP | 2007-301472 A | 11/2007 |
| JP | 2008-054608 A | 3/2008 |
| JP | 2008-104452 A | 5/2008 |
| JP | 2008-278825 A | 11/2008 |
| JP | 2009-183153 A | 8/2009 |
| JP | 2009-183154 A | 8/2009 |
| JP | 2009-183805 A | 8/2009 |
| JP | 2010-17084 A | 1/2010 |
| JP | 4764527 B1 | 9/2011 |
| JP | 4764528 B1 | 9/2011 |
| WO | 84/003304 A1 | 8/1984 |
| WO | 95/17517 A1 | 6/1995 |
| WO | 96/40970 A1 | 12/1996 |
| WO | 2009/096060 A1 | 8/2009 |
| WO | 2009/096061 A1 | 8/2009 |
| WO | 2009/096062 A1 | 8/2009 |
| WO | 2009/124240 A1 | 10/2009 |
| WO | 2010/038302 A1 | 4/2010 |
| WO | 2013/082616 A2 | 6/2013 |
| WO | 2013/082626 A2 | 6/2013 |

OTHER PUBLICATIONS

Turton, L.J. et al., "Effect of Glucose Concentration in the Growth Medium Upon Neutral and Acidic Fermentation End-products of Clostridium Bifermentans, Clostridium Sporogenes and Peptostreptococcus Anaerobius", J. Med. Microbiol., vol. 16, pp. 61-67 (1983).
Dien, B.S. et al., "Fermentation of hexose and pentose sugars using a novel ethanologenic *Escherichia coli* strain", Enzyme and Microbial Technology, vol. 23, pp. 366-371 (1998).
U.S. Office Action dated Oct. 3, 2013, issued in U.S. Appl. No. 13/782,545.
U.S. Office Action dated Aug. 19, 2013, issued in related U.S. Appl. No. 13/578,116.
English translation of JP 2009-183805 previously filed on Mar. 31, 2011, cited in U.S. Office Action U.S. Appl. No. 13/782,545.
International Search Report dated Jun. 15, 2010 for Application No. PCT/JP2010/054022.(original document submitted with IDS filed May 31, 2011).
Written Opinion of PCT/JP2010/054022, dated Jun. 15, 2010.
Office Action of Application No. 2010-536272, dated Nov. 9, 2010.
International Search Report of PCT/JP2010/054022, dated Jun. 15, 2010.
Canadian Notice of Allowance dated Aug. 22, 2013, issued in Canadian Patent Application No. 2666152.
Canadian Notice of Allowance dated Aug. 22, 2013, issued in Canadian Patent Application No. 2713529.
U.S. Office Action dated Oct. 28, 2013, issued in U.S. Appl. No. 12/443,515.
U.S. Office Action dated Oct. 7, 2013, issued in U.S. Appl. No. 13/700,753.
U.S. Restriction/Election dated Aug. 22, 2013, issued in U.S. Appl. No. 13/700,753.
Kumagai, Satoshi et al.; "Fractionation and Saccharification of Cellulose and Hemicellulose in Rice Hull by Hot-Compressed-Water Treatment with Two-Step Heating"; Journal of the Japan Institute of Energy,Dec. 1, 2003, vol. 83, pp. 776-781.
Nikkei Biobusiness; "Biomass Ethanol"; Nikkei Business Publications Inc., Nikkei Biotechnology & Business, Sep. 2002, p. 52. (English abstract).

(56) References Cited

OTHER PUBLICATIONS

Written Opinion of the International Searching Authority, issued in International Application No. PCT/JP2010/054022 with Form PCT/ISA/237.
Canadian Office Action dated Oct. 29, 2012, issued in corresponding Canadian Patent Application No. 2,741,602, (1 page).
Canadian Office Action dated Nov. 8, 2013, issued in Canadian Patent Application No. 2,801,383 (2 pages).
Canadian Notice of Allowance dated Jan. 13, 2014, issued in Canadian Patent Application No. 2,744,522 (1 page).
Indonesian Notice of Allowance dated Nov. 15, 2013, issued in Indonesian Patent Application No. W-00201002623, w/English translation, (5 pages).
U.S. Non-Final Office Action dated Dec. 17, 2013, issued in U.S. Appl. No. 13/203,929 (23 pages).
U.S. Non-Final Office Action dated Jan. 30, 2014 issued in U.S. Appl. No. 12/438,792 (39 pages).
U.S. Non-Final Office Action dated Jan. 30, 2014, issued in U.S. Appl. No. 13/578,116 (22 pages).
Gregg, D. et al., "Bioconversion of Lignocellulosic Residue to Ethanol: Process Flowsheet Development", Biomass and Bioenergy, 1995, vol. 9, No. 1-5, pp. 287-302, Cited in U.S. Office Action dated Dec. 17, 2013.
U.S. Final Office Action dated Feb. 13, 2014, issued in U.S. Appl. No. 12/865,273 (26 pages).
Liu, Chaogang, et al., "Continuous Fermentation of Hemicellulose Sugars and Cellulose to Ethanol", International Symposia on Alcohol Fuels, (2005), pp. 1-28 (cited in U.S. Final Office Action dated Feb. 13, 2014, issued in U.S. Appl. No. 12/865,273.
U.S. Non-Final Office Action issued Mar. 10, 2014, in U.S. Appl. No. 13/782,545 (27 pages).
Decision of a Patent Grant dated Mar. 4, 2014, issued in JP2009-252201 (corresponding to U.S. Appl. No. 12/443,515), w/English translation (4 pages).
Decision of a Patent Grant dated Mar. 4, 2014, issued in JP2009-245963 (corresponding to U.S. Appl. No. 12/438,792) w/English translation (4 pages).
Australian Notice of Acceptance dated Mar. 17, 2014, issued in Australian patent application No. 2011355013 (corresponding to U.S. Appl. No. 13/578,116) (2 pages).
U.S. Office Action dated Apr. 14, 2014, issued in U.S. Appl. No. 12/443,515 (16 pages).
Genta, "NEDO ni yoru Biomass Energy to Ko Koritsu Tenkan Gijutsu Kaihatsu 1), Suinetsu Bunkaiho to Koso Bunkaiho wo Kumiawaseta Nogyo Zansa to no Cellulose-kei Biomass no Tei Cost Toka Gijutsu no Kaihatsu" Clean Energy, 2010, pp. 11-15, cited in the Australian Notice of Acceptance dated Mar. 17, 2014, which was previously submitted in the IDS on Apr. 30, 2014.
Canadian Office Action dated Mar. 31, 2014, issued in Canadian Patent Application No. 2,750,753 (3 pages) (corresponding to U.S. Appl. No. 13/203,929).
U.S. Final Office Action dated May 22, 2014, issued U.S. Appl. No. 13/700,753 (40 pages).
U.S. Final Office Action dated Jun. 3, 2014, issued in U.S. Appl. No. 13/203,929 (22 pages).
International Search Report dated Jul. 3, 2012 issued in International Application No. PCT/JP2012/058460 to U.S. Appl. No. 14/381,511.
Written Opinion of the International Searching Authority dated Jul. 3, 2012 issued in International Application No. PCT/JP2012/058460 (corresponds to U.S. Appl. No. 14/381,511).
Decision of a Patent Grant dated Nov. 12, 2013, issued in Japanese Patent Application No. 2013-536355, w/English translation (corresponds to U.S. Appl. No. 14/381,511) (4 pages).
U.S. Office Action dated Apr. 24, 2015, issued in U.S. Appl. No. 14/381,511 (20 pages).
Notice of Allowance and Fee(s) Due dated Feb. 17, 2015, issued in U.S. Appl. No. 13/782,545 (20 pages).
U.S. Office Action dated Mar. 19, 2015, issued in U.S. Appl. No. 13/121,969 (21 pages).
U.S. Office Action dated Mar. 13, 2015, issued in U.S. Appl. No. 13/722,385 (41 pages).
Notice of Allowance and Fee(s) Due dated Apr. 2, 2015, issued in U.S. Appl. No. 13/132,040 (17 pages).
U.S. Office Action dated Mar. 31, 2015, issued in U.S. Appl. No. 12/865,273 (25 pages).
U.S. Office Action dated May 13, 2015, issued in U.S. Appl. No. 12/438,792 (11 pages).
U.S. Final Office Action dated Jul. 3, 2014, issued in U.S. Appl. No. 13/578,116 (17 pages).
U.S. Final Office Action dated Jun. 13, 2014, issued in U.S. Appl. No. 12/438,792 (26 pages).
U.S. Non-Final Office Action dated Aug. 27, 2014, issued in U.S. Appl. No. 13/132,040 (53 pages).
U.S. Final Office Action dated Jul. 22, 2014, issued in U.S. Appl. No. 12/443,515 (13 pages).
Office Action dated Nov. 14, 2014, issued in Indonesian Patent Application No. W00201102352, (corresponds to U.S. Appl. No. 13/121,969), w/English translation.
Office Action dated Nov. 7, 2014, issued in Indonesian Patent Application No. W00200902414, (corresponds to U.S. Appl. No. 12/438,792), w/English translation.
Genta, M. et al., "Suinetsu Bunkaiho to Koso Bunkaiho o Kumiawaseta Nogyo Zansa To no Cellulose Biomass no Tei Cost Toka Gijutsu no Kaihatsu", Heisei 21 Nendo Biomass Energy Kanren Jigyo Seika Hokokukai, Feb. 11, 2010, pp. 55-69, URL, http://www.nedo.go.jp/events/report/FF_00003.html, Cited in JP Office Action dated Oct. 14, 2014.
Lehrburger, E. "Developing biorefineries to produce energy, ethanol and other industrial products", PureVision Technology, Inc., Alternative Energy Conference, Mar. 3, 2005, pp. 1-26, Cited in U.S. Office Action dated Nov. 6, 2014.
U.S. Office Action dated Sep. 30, 2014, issued in U.S. Appl. No. 13/782,545 (43 pages).
U.S. Office Action dated Nov. 6, 2014, issued in U.S. Appl. No. 12/865,273 (27 pages).
Japanese Office Action dated Oct. 14, 2014, issued in Japanese Patent Application No. 2010-154233 (corresponds to U.S. Appl. No. 13/700,753), with English Translation (7 pages).
U.S. Office Action dated Dec. 5, 2014, issued in U.S. Appl. No. 13/121,969.
Canadian Notice of Allowance dated Dec. 5, 2014, issued in Canadian Patent Application No. 2750754 (corresponds to U.S. Appl. No. 13/203,848).
Indonesian Office Action dated Oct. 29, 2014, issued in Indonesian Patent Application No. W00201103522 (corresponds to U.S. Appl. No. 13/203,929), w/English translation.
U.S. Notice of Allowance dated Nov. 5, 2014, issued in U.S. Appl. No. 12/443,515.
U.S. Office Action dated Dec. 26, 2014, issued in U.S. Appl. No. 13/132,040.
Notice of Allowance dated Dec. 21, 2015, issued in U.S. Appl. No. 14/381,511, (11 pages).
Supplemental Notice of Allowability dated Jan. 8, 2016, issued in U.S. Appl. No. 14/381,511, (6 pages).
Notice of Allowance dated Feb. 3, 2016, issued in U.S. Appl. No. 13/578,116, (17 pages).
Decision of a Patent Grant dated Nov. 10, 2015 issued in Japan application No. 2010-154233 (counterpart to U.S. Appl. No. 13/700,753); (5 pages); with English translation.
Office Action dated Sep. 28, 2015, issued in U.S. Appl. No. 13/203,848 (34 pages).
Notice of Allowance dated Sep. 30, 2015, issued in CA 2,791,665 (counterpart to U.S. Appl. No. 13/578,116).
Office Action dated Jul. 10, 2015, issued in AUU 2012374915 (counterpart to U.S. Appl. No. 14/381,511).
Non-Final Office Action dated Jun. 19, 2015, issued in U.S. Appl. No. 13/700,753 (34 pages).
Final Office Action dated Aug. 6, 2015, issued in U.S. Appl. No. 14/381,511 (14 pages).
Notice of Allowance dated Aug. 19, 2015, issued in U.S. Appl. No. 12/438,792 (12 pages).

(56) References Cited

OTHER PUBLICATIONS

Notice of Allowance dated Aug. 12, 2015, issued in U.S. Appl. No. 13/578,116 (48 pages).
Office Action dated Aug. 21, 2015, issued in U.S. Appl. No. 13/203,929 (18 pages).
Notice of Allowance dated Jul. 6, 2015, issued in Indonesian application No. W-00201103522 (counterpart of U.S. Appl. No. 13/203,929) with English translation (4 pages).
Notice of Acceptance dated Mar. 16, 2016, issued in Australian Application No. 2012374915 (counterpart to U.S. Appl. No. 14/381,511) (2 pages).
Notice of Allowance dated Mar. 30, 2016, issued in Indonesian Patent Application No. W-00200902414 (counterpart to U.S. Appl. No. 12/438,792) with English translation. (4 pages).
Notice of Allowance dated May 5, 2016, issued in U.S. Appl. No. 13/203,848. (23 pages).
Notice of Allowance dated Mar. 14, 2016, issued in U.S. Appl. No. 13/121,969. (12 pages).
Office Action dated Sep. 29, 2016, issued in co-pending U.S. Appl. No. 14/411,473 (English; 33 pages w/ PTO-892 and returned PTO/SB/08 forms).
Notice of Allowance dated Aug. 8, 2016, issued in counterpart Indonesian Patent Application No. W00201102351, with English translation. (4 pages).
Notice of Allowance dated Oct. 5, 2016, issued in U.S. Appl. No. 13/722,385 (22 pages).

* cited by examiner

FIG.14
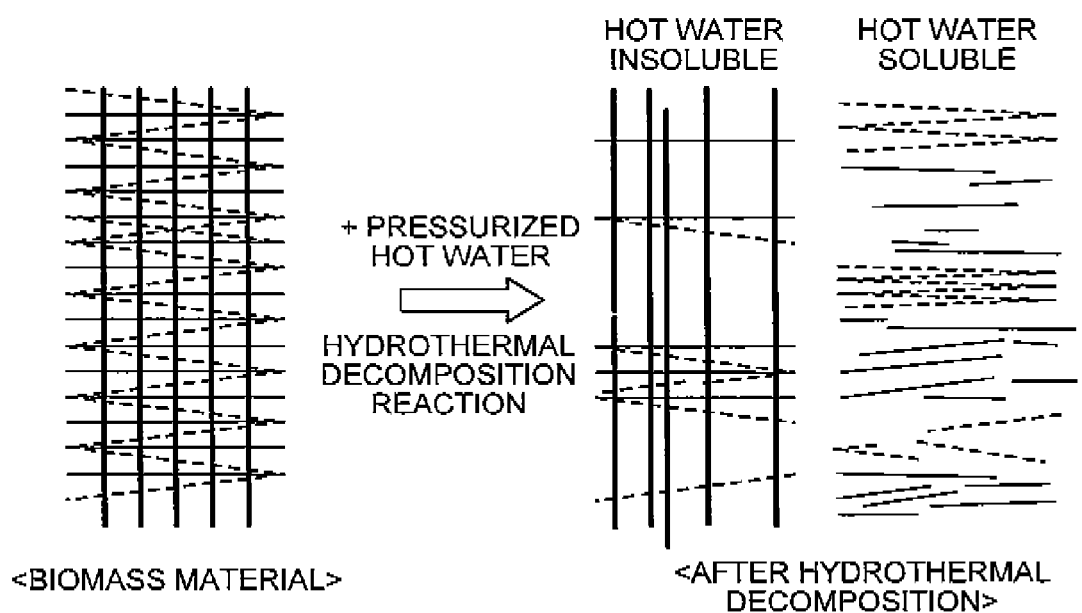
<BIOMASS MATERIAL>    <AFTER HYDROTHERMAL DECOMPOSITION>
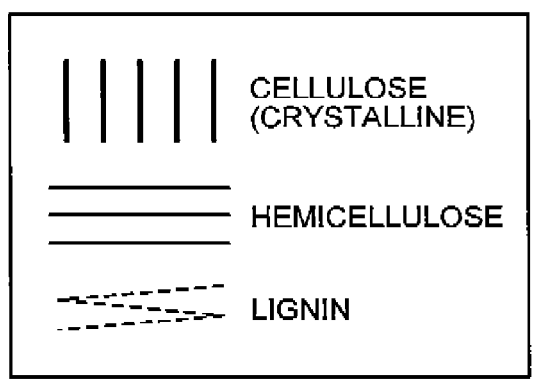

BIOMASS HYDROTHERMAL DECOMPOSITION APPARATUS, TEMPERATURE CONTROL METHOD THEREOF, AND ORGANIC RAW MATERIAL PRODUCTION SYSTEM USING BIOMASS MATERIAL

FIELD

The present invention relates to a biomass hydrothermal decomposition apparatus that can hydrothermally decompose a biomass material efficiently, a temperature control method thereof, and an organic raw material production system that uses a biomass material and can efficiently produce an organic raw material such as alcohol, substitutes for petroleum, or amino acid, the production system using the biomass hydrothermal decomposition apparatus and the method thereof.

BACKGROUND

Conventionally, a technique for producing ethanol or the like, in which solid-liquid separation is performed after saccharification of biomass such as wood by using diluted sulfuric acid or concentrated sulfuric acid, and a liquid phase is neutralized and used as a raw material for ethanol fermentation, has been practical utilized (Patent Literature 1, Patent Literature 2).

Further, production of chemical industrial raw materials (for example, lactic acid fermentation) using sugar as a starting material can be also considered.

In this specification, "biomass" represents organisms incorporated in a substance circulatory system of the global biosphere or accumulation of organic matters derived from the organisms (see JIS K 3600 1258).

Sugarcane, corn and the like, which are currently used as alcohol raw materials, are originally used as food and using these edible resources as industrial resources in a long term and in a stable manner is not preferable in view of a life cycle of effective foodstuff.

Therefore, it is an important issue to effectively use cellulose resources such as herbal biomass and wood-based biomass, which are believed to be useful industrial recourses in the future.

Further, in the cellulose resources, the resource component ratio is varied such that the ratio of cellulose is 38% to 50%, that of hemicellulose component is 23% to 32%, and that of lignin component, which is not used as a fermentation raw material, is 15% to 22%. Because industrial researches have been conducted with many unsolved problems, raw materials in the researches are assumed in a fixed manner, and currently there is no disclosure of a technique of a production system with taking the material versatility of into consideration.

Originally, because issues of waste and prevention of the global warming are taken into consideration according to a method unfavorable to fermentation feedstock as compared with starch feedstock, there is less point in the production system in which raw materials are considered in a fixed manner. This production system should be widely applicable to general waste materials. Enzymic saccharification itself is not efficient at all, and is thought to be an issue that should be solved in the future. A saccharification rate by acid treatment has a considerably small value of about 75% (on a component basis capable of being saccharified) due to excessive decomposition of sugar caused by overreaction. Therefore, the production yield of ethanol is about 25% with respect to the cellulose resources (Patent Literature 1, Patent Literature 3).

In the conventional techniques disclosed in Patent Literatures 1 to 3, there has been a phenomenon in which a reaction by-product causes inhibition of enzymic saccharification to decrease the sugar yield. Therefore, a hydrothermal decomposition apparatus that removes a substance inhibiting enzymic saccharification to increase activity of enzyme based on cellulose has been proposed (Patent Literatures 4 and 5).

CITATION LIST

Patent Literatures

Patent Literature 1: Japanese Patent Application National Publication No. H9-507386
Patent Literature 2: Japanese Patent Application National Publication No. H11-506934
Patent Literature 3: Japanese Patent Application Laid-open No. 2005-168335
Patent Literature 4: Japanese Patent Application Laid-open No. 2009-183805
Patent Literature 5: Japanese Patent Application Laid-open No. 2009-183154

Non Patent Literature

Non Patent Literature 1: Nikkei Bio Business, p. 52, September 2002

SUMMARY

Technical Problem

In the hydrothermal decomposition apparatus according to Patent Literatures 4 and 5 mentioned above, biomass and pressurized hot water are fed into counter contact with each other to cause hydrothermal reaction by internal heat exchange. However, a temperature distribution occurs at an internal temperature.

FIG. 13 is a pattern diagram of a vertical apparatus according to a conventional example that hydrothermally decomposes biomass by hot water.

As shown in FIG. 13, in this vertical hydrothermal decomposition apparatus, biomass (solid) 11 is fed into an apparatus body 42 from a bottom side and moved to an upper side by a transfer screw 43 provided therein, and a biomass solid (a hot water insoluble) 17 is discharged to outside from the upper side.

On the other hand, pressurized hot water (hereinafter, also "hot water") 15 is fed into the apparatus body 42 from the upper side and brought into counter contact with the biomass 11, and a hot-water effluent 16 is discharged to the outside from the bottom side. Therefore, in the apparatus body 42, the temperature is dropped gradually from a side for feeding the hot water 15 (upper side) toward the bottom side (a side for feeding biomass).

FIG. 14 depicts a decomposition state of biomass by hot water.

As shown in FIG. 14, biomass (cellulose raw material) includes hemicellulose and lignin other than cellulose. Specifically, the hemicellulose has a structure such that cellulose is bundled by the hemicellulose, and lignin is bonded thereto.

After hydrothermal decomposition, biomass is divided into a hot water insoluble (a solid) and a hot water soluble.

Therefore, the biomass material 11 is hydrothermally decomposed in a high temperature range (180° C. to 240° C.) by the pressurized hot water 15, and hemicellulose is dissolved and lignin is also decomposed and dissolved on the hot water side. As a result, hemicellulose and the like are dissolved on the hot water side.

In a state of hot-water solubilized hemicellulose after being solubilized in hot water, there is a problem that excessive decomposition occurs in the high temperature range (180° C. to 240° C.)

That is, when all of the hemicellulose is solubilized immediately after the biomass material 11 is input into the apparatus body and brought into contact with the pressurized hot water 15, the solubilized hemicellulose is immediately discharged to outside as the hot-water effluent 16 due to the effect of counter contact. Therefore, the excessive decomposition time is short. However, when the biomass material is raised in the pressurized hot water 15, and solubilized near a position where the biomass material is discharged as the biomass solid 17, the biomass material is brought into contact with high-temperature hot water for a long time until the biomass material is discharged from the bottom side of the apparatus body as the hot-water effluent 16. Therefore, excessive decomposition proceeds, and this causes another problem.

This excessive decomposition of hemicellulose decreases the yield of hemicellulose, which becomes a raw material of C5 sugar, and thus it is desired to suppress the excessive decomposition of hemicellulose into a hot water soluble, thereby improving plant operation efficiencies.

Further, mixing of an excessive decomposition product into hot water inhibits fermentation of C5 sugar and alcohol in the facilities on the downstream side. Therefore, it is required to prevent generation of the inhibitor.

The present invention has been achieved in view of the above problems, and an object of the present invention is to provide a biomass hydrothermal decomposition apparatus that can suppress excessive decomposition of hemicellulose as a hot water soluble, in biomass hydrothermal decomposition processing that can separate a component mainly including cellulose from a biomass material, a temperature control method, and an organic raw material production system using a biomass material.

Solution to Problem

According to an aspect of the present invention, a biomass hydrothermal decomposition apparatus that feeds a solid biomass material from one side of an apparatus body, feeds pressurized hot water from the other side, to hydrothermally decompose the biomass material while bringing the biomass material into counter contact with the pressurized hot water in the apparatus body, dissolves hot-water soluble fractions into hot water, discharges the pressurized hot water to outside from the one side of the apparatus body, and discharges the biomass material to outside from the other side, includes: an internal-temperature cooling unit that rapidly drops a temperature after performing hydrothermal decomposition for a certain period of time; a temperature measuring unit that measures an internal temperature; and a controller that controls an internal temperature to be maintained at a predetermined cooling temperature by the internal-temperature cooling unit based on a temperature measurement result obtained by the temperature measuring unit.

Advantageously, in the biomass hydrothermal decomposition apparatus, the internal-temperature cooling unit adjusts a temperature to be in a temperature drop region, in which the temperature is rapidly dropped to a temperature at which hot-water soluble fractions are not excessively decomposed, immediately after completion of hydrothermal decomposition.

Advantageously, the biomass hydrothermal decomposition apparatus, includes an internal-temperature maintaining unit formed from the other side to the one side of the apparatus body to maintain a feeding temperature of pressurized hot water for a certain period of time.

Advantageously, in the biomass hydrothermal decomposition apparatus, the internal-temperature cooling unit feeds cold water from outside or cold water obtained by heat-exchanging hot water discharged from the apparatus body by a first heat exchanger.

Advantageously, in the biomass hydrothermal decomposition apparatus, the internal-temperature maintaining unit feeds hot water from outside or hot water obtained by heat-exchanging hot water discharged from the apparatus body by a second heat exchanger.

Advantageously, in the biomass hydrothermal decomposition apparatus, a feeding temperature of the pressurized hot water is a predetermined temperature from 180° C. to 240° C., a temperature at which the hot-water soluble fractions are not excessively decomposed is 140° C. or less, and the temperature drop region is a temperature range in which a temperature is dropped from a temperature for feeding the pressurized hot water to 140° C. or less.

Advantageously, in the biomass hydrothermal decomposition apparatus, the hydrothermal decomposition apparatus is a gradient-type or vertical-type apparatus.

According to another aspect of the present invention, an organic raw material production system using a biomass material, includes: a pre-processing apparatus that pre-processes a biomass material; any one of the biomass hydrothermal decomposition apparatus described above; a first enzymatic decomposition device that processes, with an enzyme, cellulose in a biomass solid discharged from the biomass hydrothermal decomposition apparatus to decompose cellulose into a sugar solution containing hexose with the enzyme; and a fermentation device that produces any one of alcohol, substitutes for petroleum, and amino acid by fermentative treatment, by using a sugar solution obtained by the first enzymatic decomposition device.

Advantageously, the organic raw material production system using a biomass material includes: a second enzymatic decomposition device that processes, with an enzyme, hemicellulose in a hot-water effluent to decompose hemicellulose into a sugar solution containing pentose with the enzyme; and a fermentation device that produces any one of alcohol, substitutes for petroleum, and amino acid by fermentative treatment, by using a second sugar solution obtained by the second enzymatic decomposition device.

Advantageously, the organic raw material production system using a biomass material includes: a sulfuric-acid decomposition device that decomposes, with sulfuric acid, a hemicellulose component in a hot-water effluent discharged from the hydrothermal decomposition apparatus to decompose the hemicellulose component into a second sugar solution containing pentose; and a second fermentation device that produces any one of alcohol, substitutes for petroleum, and amino acid by fermentative treatment, by using a second sugar solution obtained by the sulfuric-acid decomposition device.

According to the present invention, a hydrothermal decomposition is efficiently performed, and a temperature is quickly dropped by an internal-temperature cooling unit that quickly drops the temperature, thereby suppressing an excessive decomposition of hydrothermally solubilized hemicelluloses, which is solubilized fractions. Accordingly, an excessive decomposition of hemicelluloses which is hydrothermally solubilized fractions is suppressed, and a decrease in the yield of C5 sugar is reduced.

BRIEF DESCRIPTION OF DRAWINGS

FIG. 14 depicts a decomposition state of biomass by hot water.

DESCRIPTION OF EMBODIMENTS

Exemplary embodiments of the present invention will be explained below in detail with reference to the accompanying drawings. The present invention is not limited to the embodiments. In addition, constituent elements in the following embodiments include those that can be easily assumed by persons skilled in the art or that are substantially equivalent.

First Embodiment

A biomass hydrothermal decomposition apparatus according to an embodiment of the present invention is explained with reference to the drawings.

Figure 1A:
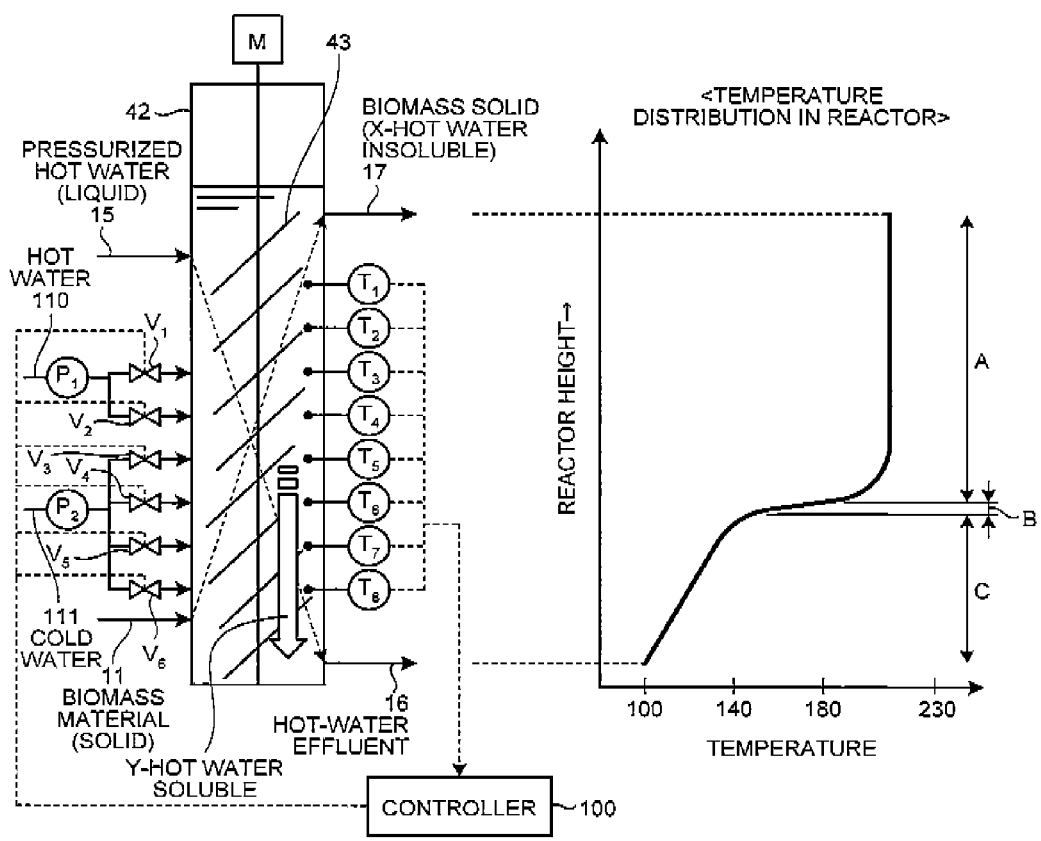
FIG. 1A is a conceptual diagram of a hydrothermal decomposition apparatus according to a first embodiment of the present invention and a temperature distribution.
Figure 1B:
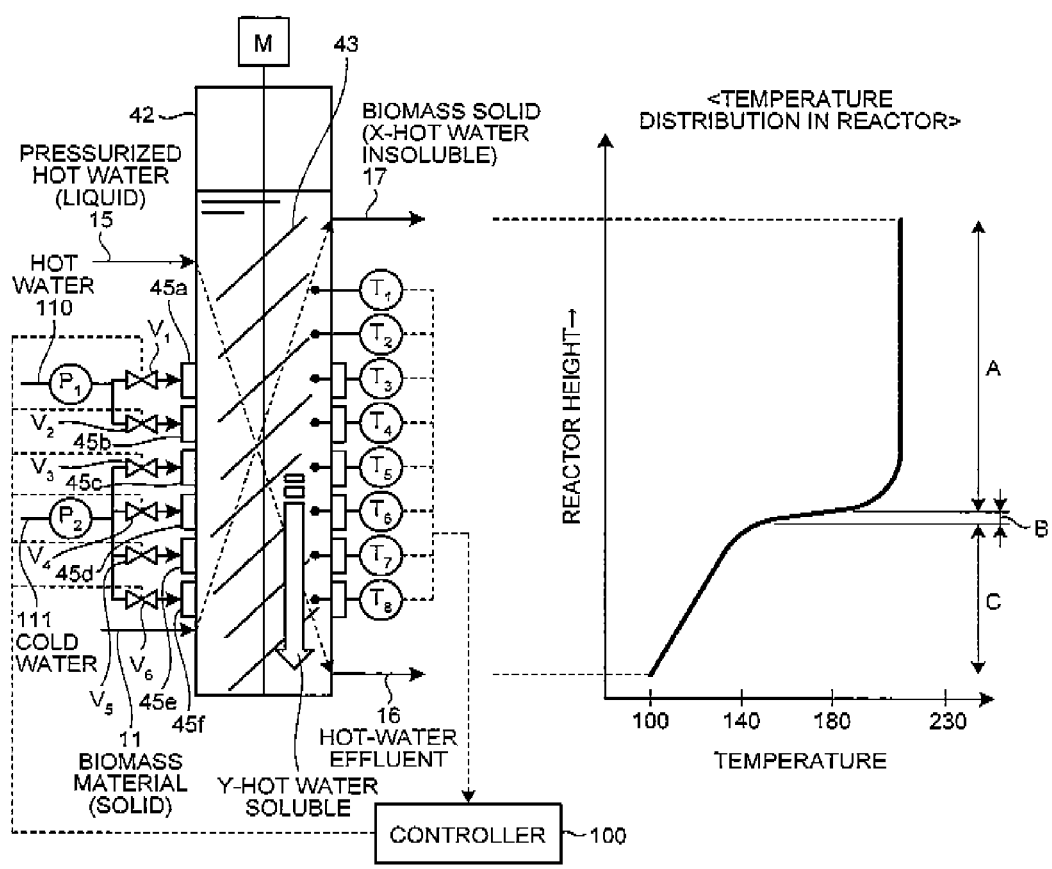
FIG. 1B is a conceptual diagram of the hydrothermal decomposition apparatus according to the first embodiment and a temperature distribution.

FIG. 1A is a conceptual diagram of a biomass hydrothermal decomposition apparatus according to a first embodiment and a temperature distribution. FIG. 1B is a conceptual diagram of another biomass hydrothermal decomposition apparatus according to the first embodiment and a temperature distribution.

As shown in FIG. 1A, the biomass hydrothermal decomposition apparatus according to the present embodiment feeds the solid biomass material 11 from one side of an apparatus body 42 by a transfer screw 43, and feeds the pressurized hot water 15 from the other side, to hydrothermally decompose the biomass material 11 while bringing the biomass material 11 into counter contact with the pressurized hot water 15 in the apparatus body 42. Further, the biomass hydrothermal decomposition apparatus dissolves hot-water soluble fractions (hemicellulose components) in hot water, discharges the pressurized hot water to outside from the one side of the apparatus body 42 as a hot-water effluent 16, and discharges the biomass solid (a hot water insoluble) 17 to outside from the other side. The biomass hydrothermal decomposition apparatus includes an internal-temperature cooling unit that rapidly drops the temperature after performing hydrothermal decomposition for a certain period of time, temperature measuring units $T_1$ to $T_8$ that measure an internal temperature, and a controller 100 that controls the internal temperature to be maintained at a predetermined cooling temperature by the internal-temperature cooling unit based on temperature measurement results obtained by temperature measuring units $T_1$ to $T_8$.

In the present embodiment, the biomass hydrothermal decomposition apparatus includes an internal-temperature maintaining unit that adjusts the temperature to be in an effective reaction region (a hydrothermal decomposition region) A formed from the other side to the one side of the apparatus body 42 of the biomass hydrothermal decomposition apparatus, in which a feeding temperature of the pressurized hot water 15 (180 to 240° C., such as 200° C.) is maintained for a certain period of time to cause hydrothermal decomposition, in order to maintain a favorable hydrothermal reaction temperature.

In the present embodiment, the internal-temperature maintaining unit feeds hot water 110 from outside, and the internal-temperature cooling unit feeds cold water 111 from outside.

In the drawings, reference numeral 100 denotes the controller, reference signs $V_1$ to $V_6$ denote ON-OFF valves, reference sign $P_1$ denotes a hot-water feed pump, and reference sign $P_2$ denotes a cold-water feed pump.

The predetermined cooling temperature is a temperature at which hemicellulose as hot-water soluble fractions is not excessively decomposed, and preferably, it is 140° C. or less, for example.

Accordingly, the internal-temperature cooling unit forms a temperature drop region (a dissolved-hemicellulose excessive decomposition suppressing region) B by rapidly dropping the temperature from the hydrothermal reaction temperature to the temperature at which hemicellulose as hot-water soluble fractions is not excessively decomposed (for example, from 200° C. to 140° C.)

The internal-temperature maintaining unit maintains the effective reaction region (the hydrothermal decomposition region) A at a predetermined temperature by the internal-temperature maintaining unit. Further, the internal-temperature cooling unit adjusts the temperature to form the temperature drop region (the dissolved-hemicellulose excessive decomposition suppressing region) B, in which the temperature is rapidly dropped to a temperature (for example, 140°

C. or less) at which the hot-water soluble fractions are not excessively decomposed (for example, from 200° C. to 140° C.), immediately after it is out of the effective reaction region A, thereby suppressing excessive decomposition of hot-water solubilized hemicellulose, which becomes a solubilized fraction.

In the present embodiment, the internal-temperature maintaining unit is provided. However, when the temperature inside the apparatus is maintained constant for a predetermined time, the internal-temperature maintaining unit is not required, and installation thereof can be determined according to the characteristics of the apparatus.

Figure 5:
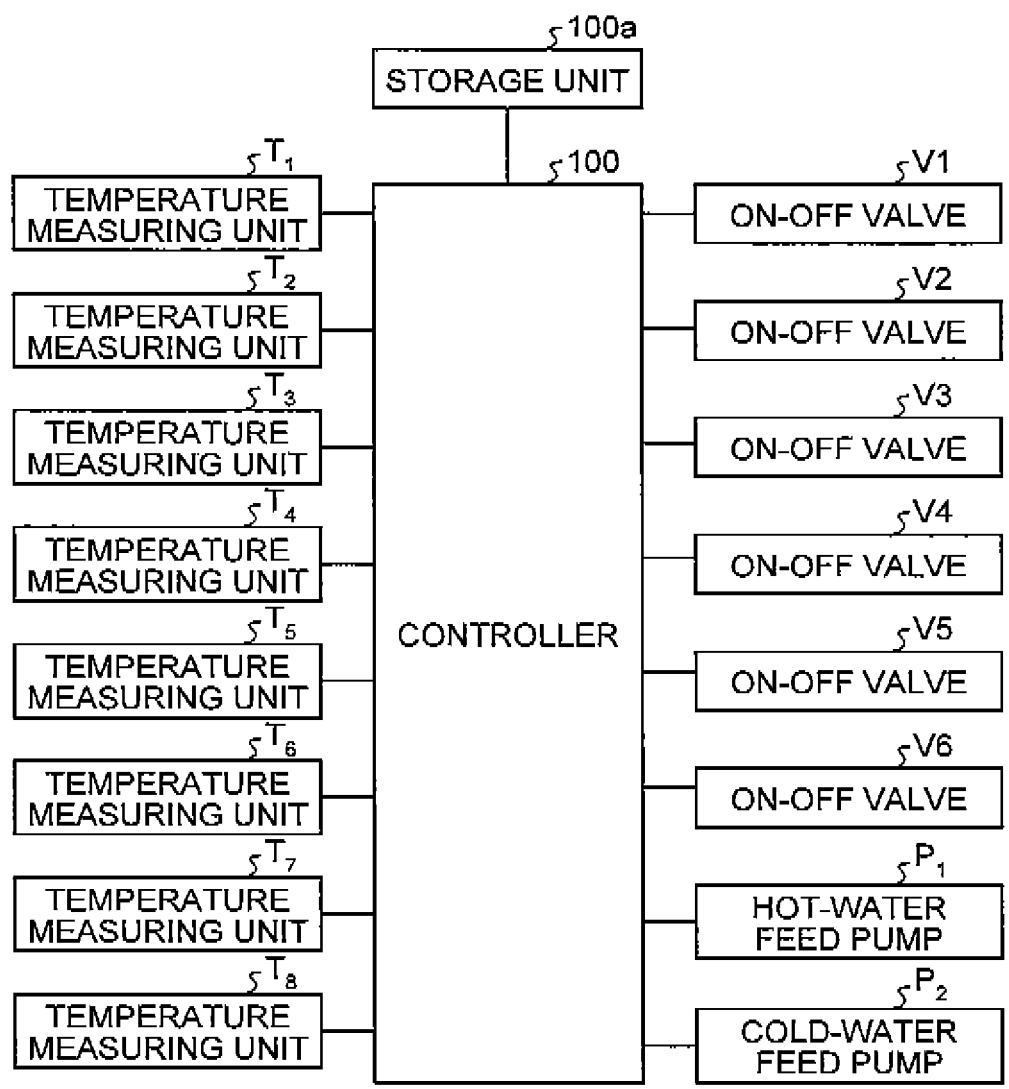
FIG. 5 is a block diagram of a control system according to the embodiment of the present invention.
Figure 6:
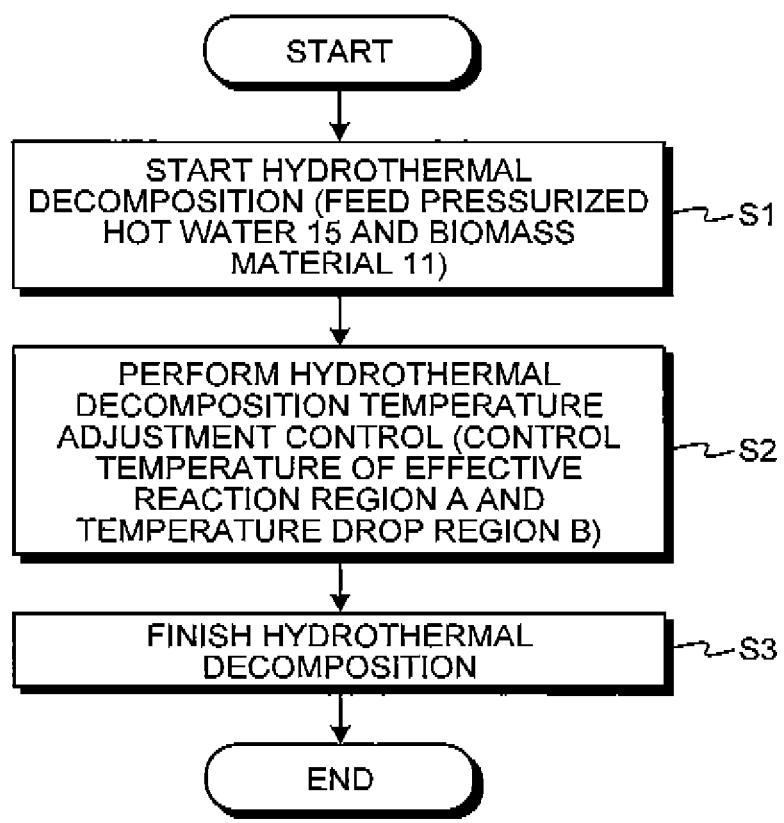
FIG. 6 is a flowchart of control.

FIG. 5 is a block diagram of a control system according to the embodiment of the present invention, and FIG. 6 is a flowchart of control.

The controller 100 shown in FIG. 1 is constituted by a microcomputer or the like. As shown in FIG. 5, the controller 100 includes a storage unit 100a. The storage unit 100a is constituted by a RAM, a ROM and the like, and stores programs and data.

The storage unit 100a stores data of the biomass material 11 and the pressurized hot water 15 to operate the biomass hydrothermal decomposition apparatus. In this data, for example, the feeding temperature of the biomass material 11 is set to 100° C. The feeding temperature of the pressurized hot water 15 is also set to 200° C., for example. The effective reaction region (the hydrothermal decomposition region) A for effecting hydrothermal decomposition is set to 200° C. same as the feeding temperature of the pressurized hot water 15, and a reaction time is set to a predetermined time from 5 to 20 minutes. The reaction time is appropriately changed according to the kind of biomass material. The temperature drop region (the dissolved-hemicellulose excessive decomposition suppressing region) B is set so that the temperature is rapidly dropped from 180° C. to 140° C. The controller 100 is connected with the temperature measuring units $T_1$ to $T_8$, the ON-OFF valves $V_1$ to $V_6$, the hot-water feed pump $P_1$, and the cold-water feed pump $P_2$.

In the present embodiment, the ON-OFF valves $V_1$ and $V_2$ feed the hot water 110, and the ON-OFF valves $V_3$ to $V_6$ feed the cold water 111.

The controller 100 performs integrated control of the ON-OFF valves $V_1$ to $V_6$, the hot-water feed pump $P_1$, and the cold-water feed pump $P_2$ according to the programs and data stored in the storage unit 100a beforehand, based on internal temperature information input from the temperature measuring units $T_1$ to $T_8$.

As shown in FIG. 6, the controller 100 feeds the pressurized hot water 15 and the biomass material 11 to start hydrothermal decomposition of the biomass material 11, based on a biomass hydrothermal decomposition start command (Step S1).

Accordingly, the controller 100 performs hydrothermal-decomposition temperature adjustment control including temperature control for forming the effective reaction region (the hydrothermal decomposition region) A in which the biomass material 11 is hydrothermally decomposed while the biomass material 11 and the pressurized hot water 15 are brought into counter contact with each other in the apparatus body 42, and the feeding temperature (200° C.) of the pressurized hot water 15 is maintained for a certain period of time to cause hydrothermal decomposition, and temperature control for forming the temperature drop region (the dissolved-hemicellulose excessive decomposition suppressing region) B in which the temperature is rapidly dropped (for example, from 200° C. to 140° C.) to a temperature at which the hot-water soluble fractions are not excessively decomposed (for example, 140° C.), immediately after it is out of the effective reaction region A (Step S2).

When the hydrothermal decomposition reaction is complete, feed of the biomass material 11 and the pressurized hot water 15 is stopped to finish hydrothermal decomposition (Step S3).

At Step S2, in the temperature control of the temperature drop region (the dissolved-hemicellulose excessive decomposition suppressing region) B, the controller 100 controls an injection amount of the cold water 111 by appropriately opening and closing the ON-OFF valves $V_3$ to $V_6$ for each injection position of the cold water 111 so that the length of the temperature drop region (the dissolved-hemicellulose excessive decomposition suppressing region) B, that is, the remaining time of a hot water soluble in the temperature drop region B is minimized.

At Step S2, when the reaction time is short or temperature drop is small, because control of the effective reaction region (the hydrothermal decomposition region) A for effecting hydrothermal decomposition is appropriately performed, feed of the hot water 110 may not be required when a certain temperature can be maintained.

In installation of the internal-temperature maintaining unit and the internal-temperature cooling unit, which are temperature adjusting units of the present invention, when modeling of mixed state for hydrothermal decomposition in the apparatus body is performed, the idea of a continuous tank-type reactor model can be applied.

In the continuous tank-type reactor model, a mixing characteristic of the apparatus body as a reactor is modeled virtually in a state with a plurality of small perfect mixing chambers being serially connected.

The number (N) of the perfect mixing chambers changes according to the characteristics of individual apparatus body. However, when the N of the apparatus bodies actually installed is determined, it is desired to install the internal-temperature maintaining units and the internal-temperature cooling units in the number more than N.

As a temperature adjusting method, a direct temperature-adjusting method of directly feeding refrigerant (cold water) 111 or the hot water 110 as shown in FIG. 1A, and an indirect temperature-adjusting method using multistage jackets 45a to 45f as shown in FIG. 1B can be exemplified.

When the hot water 110 or the cold water 111 is directly fed into the apparatus body 42, concentration in the apparatus body 42 changes, and thus it is desired to use the indirect temperature-adjusting method in order to avoid a change in concentration.

In this manner, in the present embodiment, a temperature same as the temperature (for example, 200° C.) for feeding the pressurized hot water 15 is maintained by the internal-temperature maintaining unit by performing temperature control by the controller 100 so that the internal temperature becomes a predetermined temperature by the internal-temperature maintaining unit and the internal-temperature cooling unit, based on the temperature measurement results obtained by the temperature measuring units $T_1$ to $T_8$, thereby performing the hydrothermal decomposition efficiently. To suppress excessive decomposition of hot-water solubilized hemicellulose, which becomes a solubilized fraction by hydrothermal decomposition, immediately after completion of hydrothermal decomposition, the internal-temperature cooling unit rapidly cools the temperature so as to form the temperature drop region (the dissolved-hemicellulose excessive decomposition suppressing region) B in which the temperature is rapidly dropped from the hydrothermal decomposition temperature (200° C.) to the temperature at which excessive decomposition does not proceed (140° C.), thereby enabling to suppress excessive decomposition of dissolved hemicellulose considerably. Accordingly, a decrease in the yield of C5 sugar can be reduced.

Figure 2:
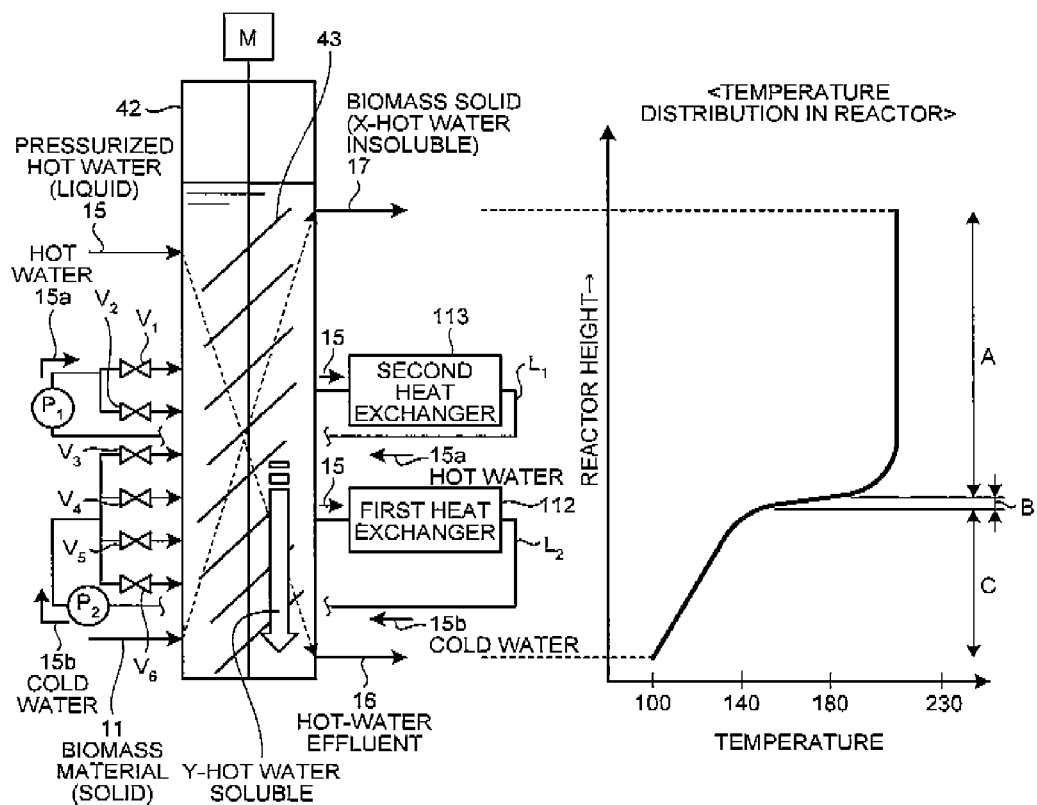
FIG. 2 is a conceptual diagram of another biomass hydrothermal decomposition apparatus according to the first embodiment and a temperature distribution.

FIG. 2 is a conceptual diagram of another biomass hydrothermal decomposition apparatus according to the first embodiment and a temperature distribution.

When the cold water 111 or the hot water 110 is fed from outside, concentration in the apparatus body 42 is diluted.

Therefore, in the present embodiment, as shown in FIG. 2, when cold water is fed, a part of the pressurized hot water 15 can be discharged from the apparatus body 42 and cooled to a predetermined temperature by a first heat exchanger 112 to become cold water 15b, which is then fed into the apparatus body 42 again via a circulation line $L_2$. A part of the hot water 15 can be discharged to outside once from the apparatus body 42 and adjusted to a predetermined temperature by a second heat exchanger 113, and heat-exchanged hot water 15a can be fed into the apparatus body 42 again via the circulation line $L_1$.

Accordingly, because there is no change in concentration in the apparatus body 42, intended hydrothermal decomposition can be performed.

Figure 3:
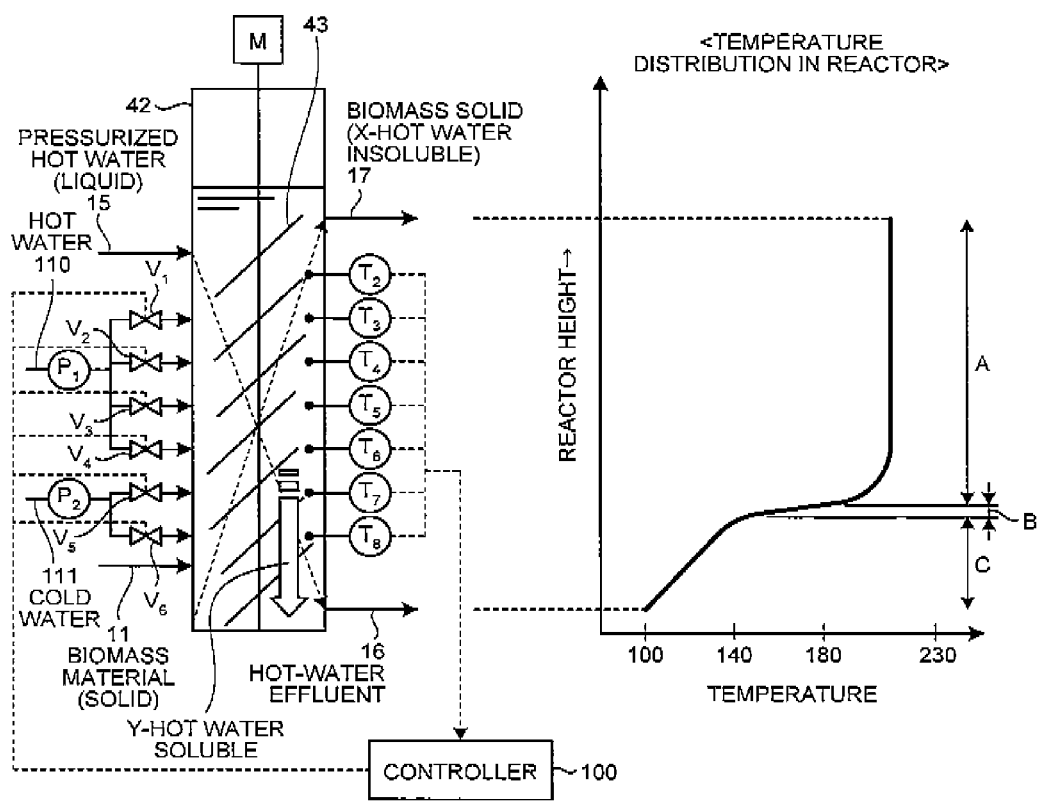
FIG. 3 is a conceptual diagram of another biomass hydrothermal decomposition apparatus according to the first embodiment and a temperature distribution.

FIG. 3 is a conceptual diagram of another biomass hydrothermal decomposition apparatus according to the first embodiment and a temperature distribution. In the present embodiment, as shown in FIG. 3, the pressurized hot water 15 is fed at four positions so that the hot water 110 is fed to the lower part of the apparatus body 42, thereby forming the effective reaction region (the hydrothermal decomposition region) A in almost the entire area of the apparatus body 42. The cold water 111 is fed from two positions in a lower part of the apparatus body 42, thereby forming the temperature drop region (the dissolved-hemicellulose excessive decomposition suppressing region) B. As a result, a part of the temperature measuring unit $T_1$ can be omitted as compared with the apparatus shown in FIG. 1A, thereby enabling to decrease the tank height of the apparatus body 42 and to downsize the apparatus body 42.

Figure 4:
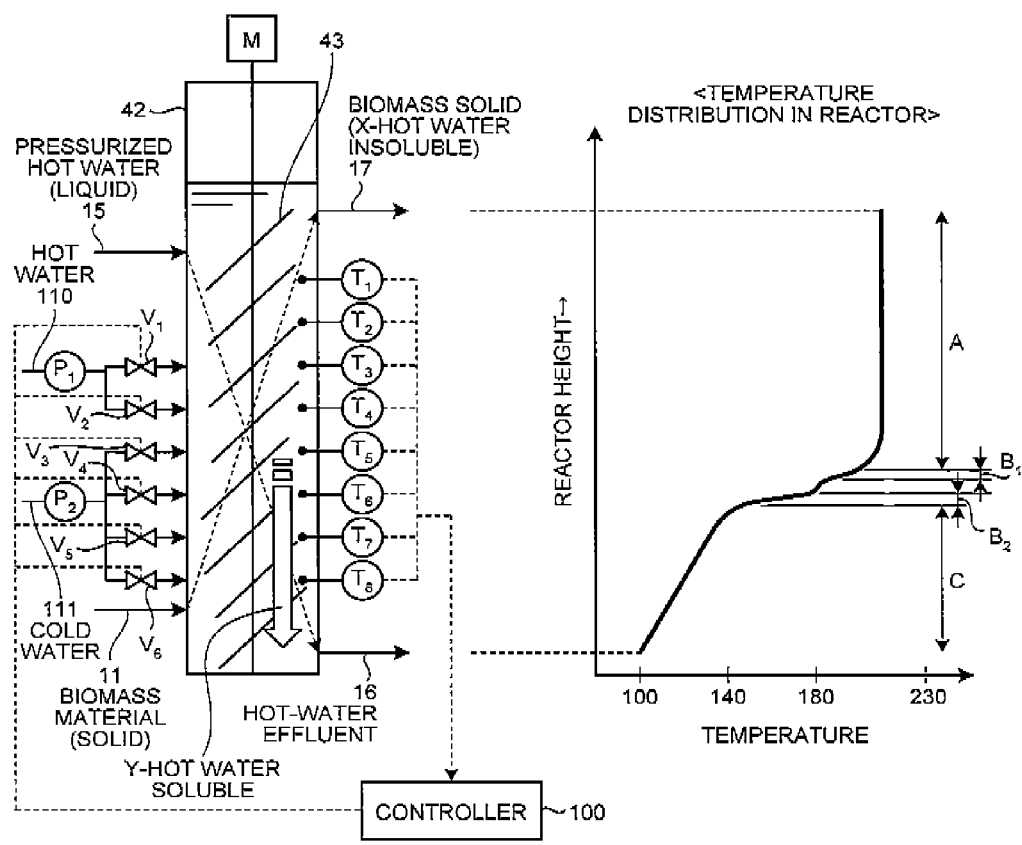
FIG. 4 is a conceptual diagram of another biomass hydrothermal decomposition apparatus according to the first embodiment and a temperature distribution.

FIG. 4 is a conceptual diagram of another biomass hydrothermal decomposition apparatus according to the first embodiment and a temperature distribution. As shown in FIG. 4, when the temperature of the effective reaction region (the hydrothermal decomposition region) A is 180° C. or higher (for example, 200° C.), the temperature (200° C.) of the effective reaction region is maintained for a predetermined time, and thereafter a first temperature drop region $B_1$ in which the temperature is dropped to 180° C., and a second temperature drop region $B_2$ in which the temperature is cooled to a temperature at which excessive decomposition does not occur (the temperature is dropped from 180° C. to 140° C.) immediately thereafter can be provided.

This is because, for example, when the hemicellulose component is saccharified to pentose, a different type of sugar such as arabinose and xylose may dissolve at a temperature lower than 200° C. Accordingly, hemicellulose components changing to arabinose dissolve at a low temperature (180° C.). Therefore, it is possible to have a configuration such that these components are dissolved first at a temperature around 180° C., and then hemicellulose components changing to xylose are dissolved at a higher temperature (200° C.)

Hemicellulose dissolved in the pressurized hot water 15 passes the temperature drop region (the dissolved-hemicellulose excessive decomposition region) B in which the pressurized hot water 15 flows downward immediately after dissolution within a short time, thereby decreasing excessive decomposition.

In the present invention, the reason why the temperature is dropped to 140° C. or less as the temperature for suppressing excessive decomposition is explained with reference to the graph of xylose reduction rate in the hot water soluble shown in FIG. 12.

Figure 12:
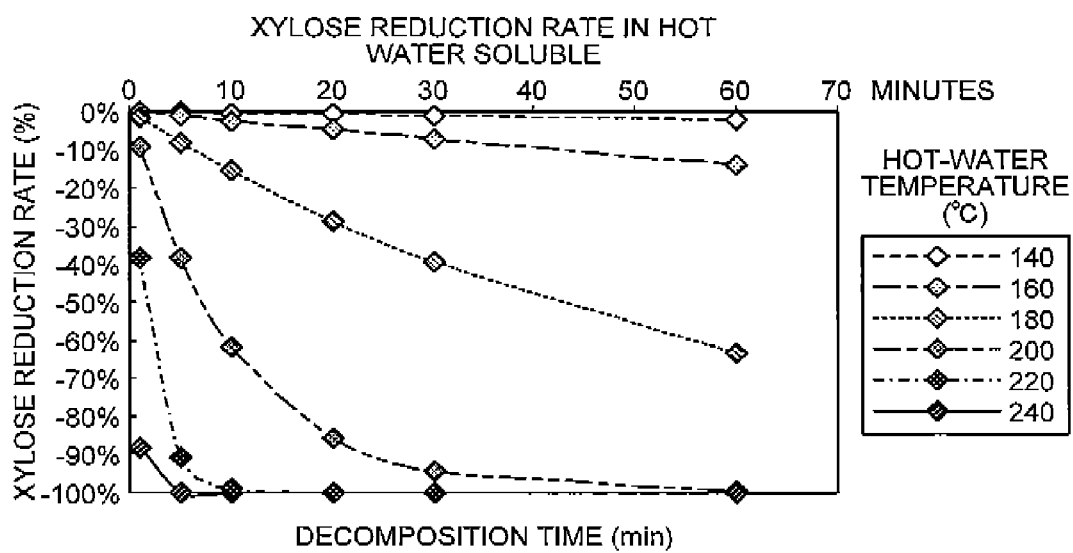
FIG. 12 depicts a relation between a xylose reduction rate in hot water soluble and a decomposition time.
Figure 13:
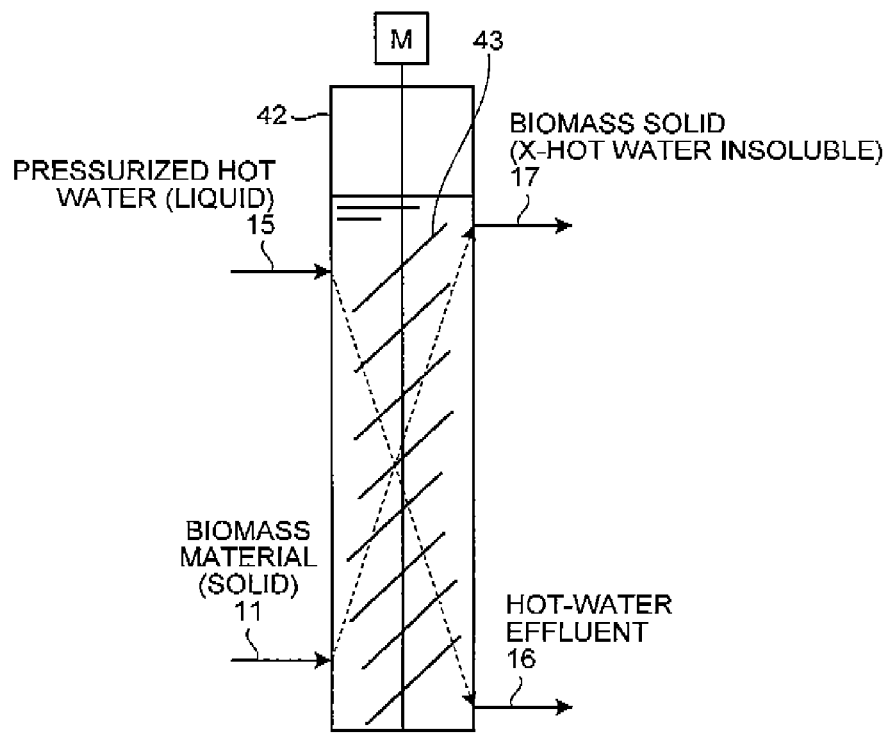
FIG. 13 is a pattern diagram of a vertical apparatus according to a conventional example that hydrothermally decomposes biomass by hot water.

As shown in FIG. 12, the temperature range of 140° C. or more is a range in which hemicellulose, which is a hot-water solubilized component, is excessively decomposed.

Figure 9:
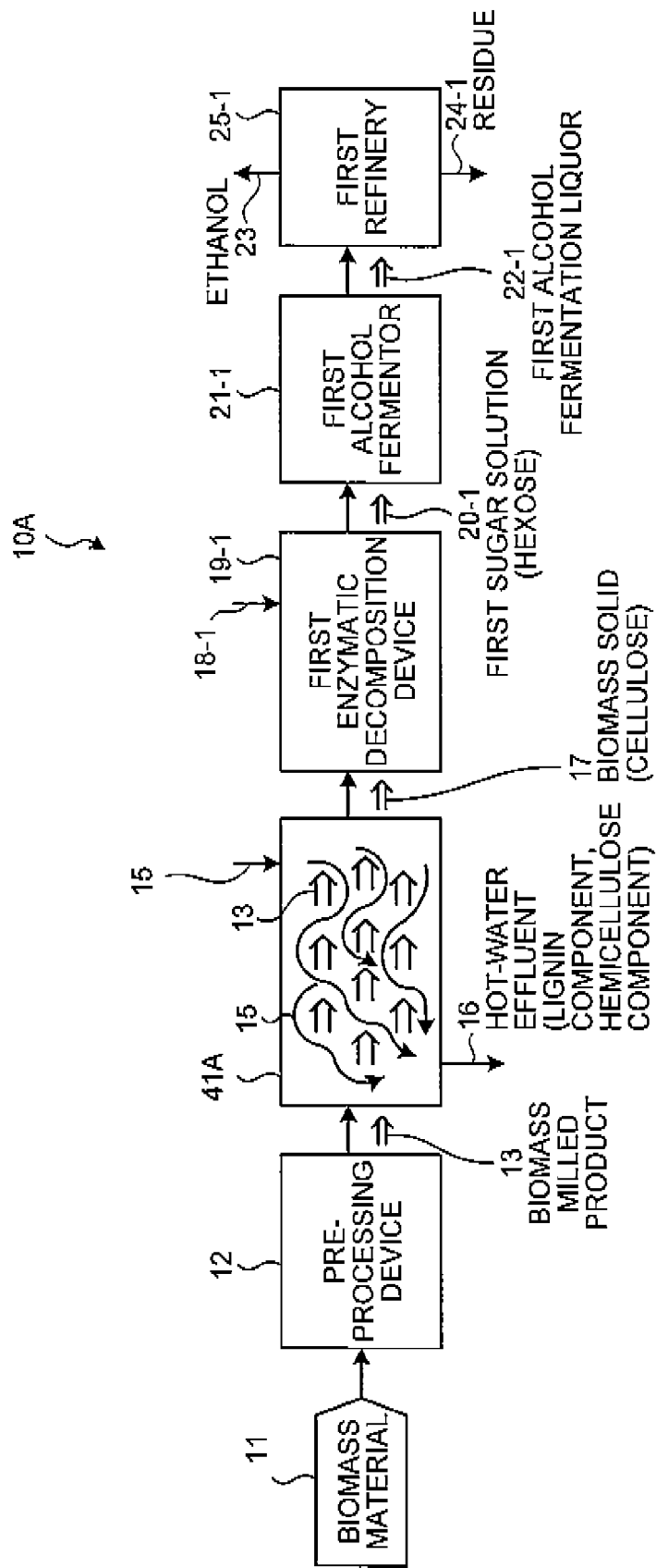
FIG. 9 is a schematic diagram of a production system of alcohol as an organic material using a biomass material according to a fourth embodiment of the present invention.

In FIG. 12, a decomposition state with a passage of time of hemicellulose solubilized in hot water at each temperature is confirmed by using hot water in which hemicellulose is once dissolved from biomass. Because hemicellulose cannot be directly measured, FIG. 9 depicts a rate of decrease after hemicellulose is converted to C5 sugar (xylose).

As described above, in a state of hot-water solubilized hemicellulose after being solubilized in hot water (in a so-called naked state), because excessive decomposition occurs in a temperature range equal to or higher than 140° C., hemicellulose needs to be cooled quickly up to 140° C. or lower as in the present invention.

If the discharging temperature of the hot-water effluent 16 to be discharged from the apparatus body is made 140° C. or lower by cooling, the hot-water effluent 16 can be directly discharged. However, for example, the apparatus can have a gradual cooling region C in which the hot-water effluent 16 is gradually cooled to about 100° C. to 120° C., for example, and the hot-water effluent 16 is transferred to the next process.

The reaction time in temperature control of the effective reaction region (the hydrothermal decomposition region) A is preferably 20 minutes or less, and more preferably from 5 to 15 minutes. This is because if reaction is performed for a long time, hemicellulose dissolved in hot water accumulates to increase the rate of the excessive decomposition product, which is not desirable.

As a reaction pressure, it is desired that a pressure higher by 0.1 to 0.5 megapascal is applied to a saturated vapor pressure of water at each temperature of the reaction temperature (180° C. to 240° C.) of the apparatus body 42A.

According to the present invention, the pressurized hot water 15 and the biomass material 11 are brought into counter contact with each other, and the biomass material 11 is washed by the pressurized hot water 15 on an upper end side from which the biomass solid 17 is discharged. Even when the excessive decomposition component is present, taking out of the biomass material 11 to outside in the solid state is reduced by the washing effect, thereby purifying the biomass solid 17. Accordingly, a raw material of hexose that hardly causes reaction inhibition can be obtained.

Second Embodiment

A specific example of the biomass hydrothermal decomposition apparatus according to the present invention is explained with reference to the drawings.

Figure 7:
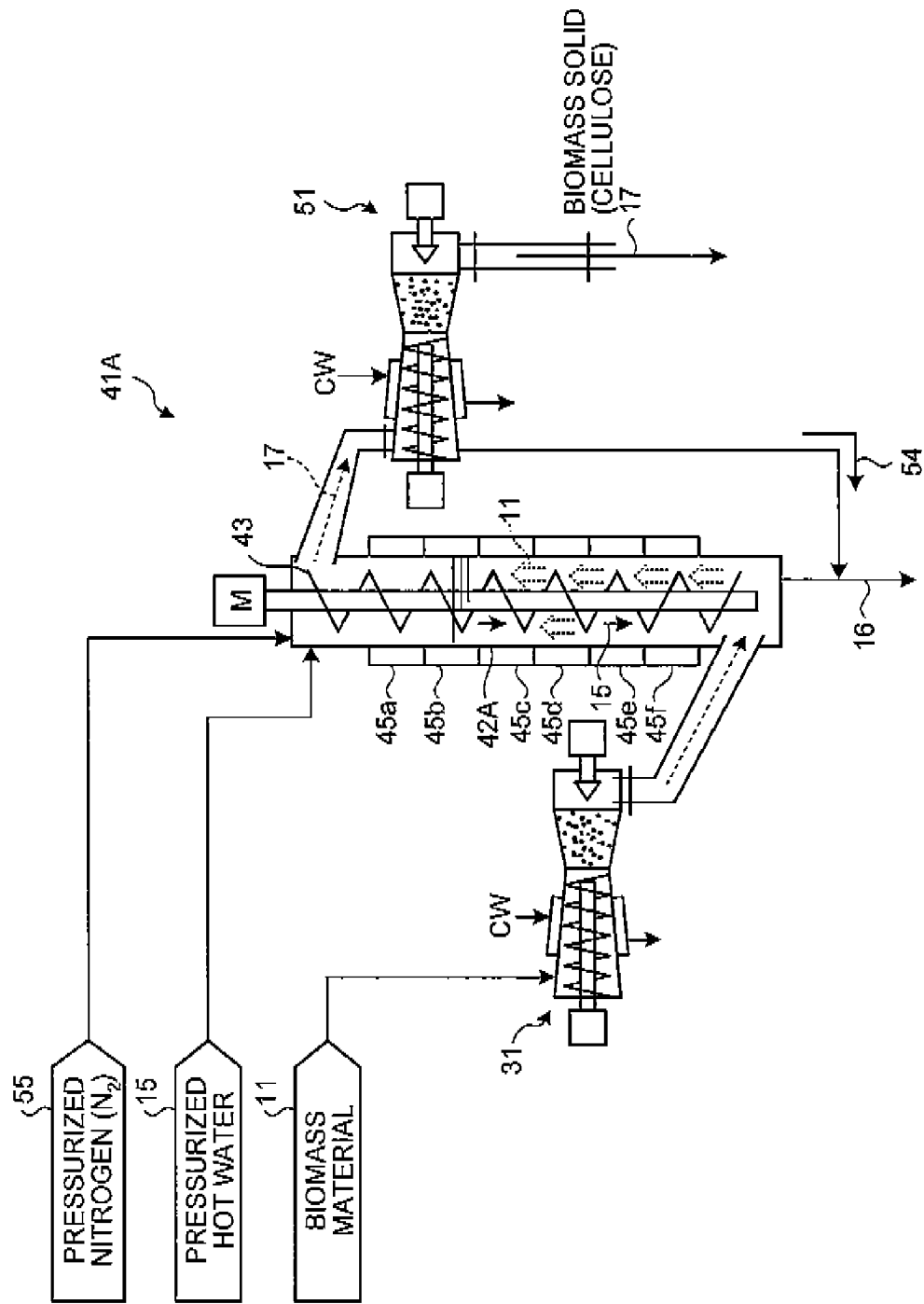
FIG. 7 is a schematic diagram of a hydrothermal decomposition apparatus according to a second embodiment of the present invention.

FIG. 7 is a schematic diagram of a biomass hydrothermal decomposition apparatus according to a second embodiment.

As shown in FIG. 7, a hydrothermal decomposition apparatus 41A according to the present embodiment includes: a biomass feeding device 31 that feeds the biomass material 11 under a normal pressure to under an increased pressure; and the hydrothermal decomposition apparatus 41A that gradually transports the fed biomass material 11 (in the present embodiment, for example, wheat straw) from a lower end side into the vertical apparatus body (hereinafter, "apparatus body") 42A by the transfer screw 43, feeds the pressurized hot water 15 from an upper end side different from a feed position of the biomass material 11 into the apparatus body 42A, hydrothermally decomposes the biomass material 11 while bringing the biomass material 11 into counter contact with the pressurized hot water 15, and transfers a lignin component and a hemicellulose component into the pressurized hot water 15 to separate the lignin component and the hemicellulose component from the biomass material 11. The hydrothermal decomposition apparatus 41A also includes a biomass discharging device 51 that discharges the biomass solid 17 from the upper end side of the apparatus body 42A under an increased pressure to under a normal pressure. In FIG. 4, reference numeral 54 denotes dehydration liquid and reference numeral 55 denotes pressurized nitrogen.

By using the hydrothermal decomposition apparatus 41A, the biomass material 11 and the pressurized hot water 15 are brought into counter contact with each other in the apparatus. As a result, the biomass solid 17 mainly including cellulose can be obtained, by transferring a side reaction product (lignin component and hemicellulose component) other than the hydrothermal reaction for generating cellulose (which becomes hexose solution by enzymatic saccharification), which is a target component, into the pressurized hot water 15.

At this time, a temperature jacket, which is a temperature adjusting apparatus of the apparatus body 41A, is divided into a plurality of elements 45a to 45f constituted by heating-medium feeding units 45a to 45d and cooling-medium feeding units 45e to 45f.

Temperature control for maintaining a predetermined temperature (for example, 200° C.) with the pressurized hot water 15 being fed is then performed by feeding a heating medium at a predetermined temperature in the heating-medium feeding units 45a to 45d, thereby efficiently effecting hydrothermal decomposition.

Thereafter, temperature control is performed to drop the temperature quickly from the hydrothermal decomposition temperature (200° C.) to a temperature (140° C.) at which excessive decomposition does not proceed, by feeding a cooling medium at a predetermined temperature in the cooling-medium feeding units 45e to 45f, in order to suppress excessive decomposition of the hydrothermally solubilized hemicellulose, which has become solubilized fractions due to the cooling medium. Therefore, excessive decomposition of hemicellulose, which is a hydrothermally solubilized component, is suppressed. Accordingly, a decrease in the yield of C5 sugar is reduced.

As a result, with the biomass solid 17, cellulose can be efficiently saccharified to a first sugar solution containing hexose, thereby enabling to efficiently produce various organic materials (for example, alcohol) from the sugar solution.

On the other hand, the hemicellulose component in the hot-water effluent 16 discharged from the hydrothermal decomposition apparatus 41A can be saccharified to a second sugar solution containing pentose, thereby enabling to efficiently produce various organic materials (for example, alcohol) from the sugar solution.

In the present embodiment, while the biomass material 11 is fed from the lower end side, the present invention is not limited thereto. Conversely, the biomass material 11 can be fed from the upper end side. At this time, the pressurized hot water 15 is fed from the lower end side.

The biomass feeding device 31 that feeds the biomass under a normal pressure to under an increased pressure includes a pump unit such as a piston pump or a slurry pump.

In the present embodiment, the hydrothermal decomposition apparatus 41A is a vertical apparatus as shown in FIG. 4. However, the present invention is not limited thereto, and a gradient-type or horizontal-type hydrothermal decomposition apparatus can be used.

The reason why the hydrothermal decomposition apparatus is the gradient type or vertical type is that gas generated in the hydrothermal decomposition reaction and gas brought into a raw material can quickly escape from above, which is preferable. Further, because the decomposition product is discharged by the pressurized hot water 15, concentration of the discharged product increases from the upper side toward the lower side, which is preferable in view of the discharging efficiency.

In the hydrothermal decomposition apparatus 41A according to the present embodiment, by providing the transfer screw 43, (1) the solid can be transported in a solid-liquid counter flow; (2) solid liquid separation becomes possible in the apparatus body 42A; and (3) mixture of the pressurized hot water 15 on the surface of the solid and inside the solid is progressed in the apparatus body 42A to facilitate reaction.

Further, a scraper (not shown) that prevents clogging of an discharging hole of the hot-water effluent 16 can be provided in the transfer screw 43.

In the present embodiment, a temperature jacket has been explained as an example of the temperature adjusting apparatus. However, the present invention is not limited thereto, and for example, a method of injecting cold water or a temperature adjusting method by external heat exchange can be appropriately used.

Third Embodiment

Another embodiment of the biomass hydrothermal decomposition apparatus according to the present invention is explained with reference to the drawings.

Figure 8:
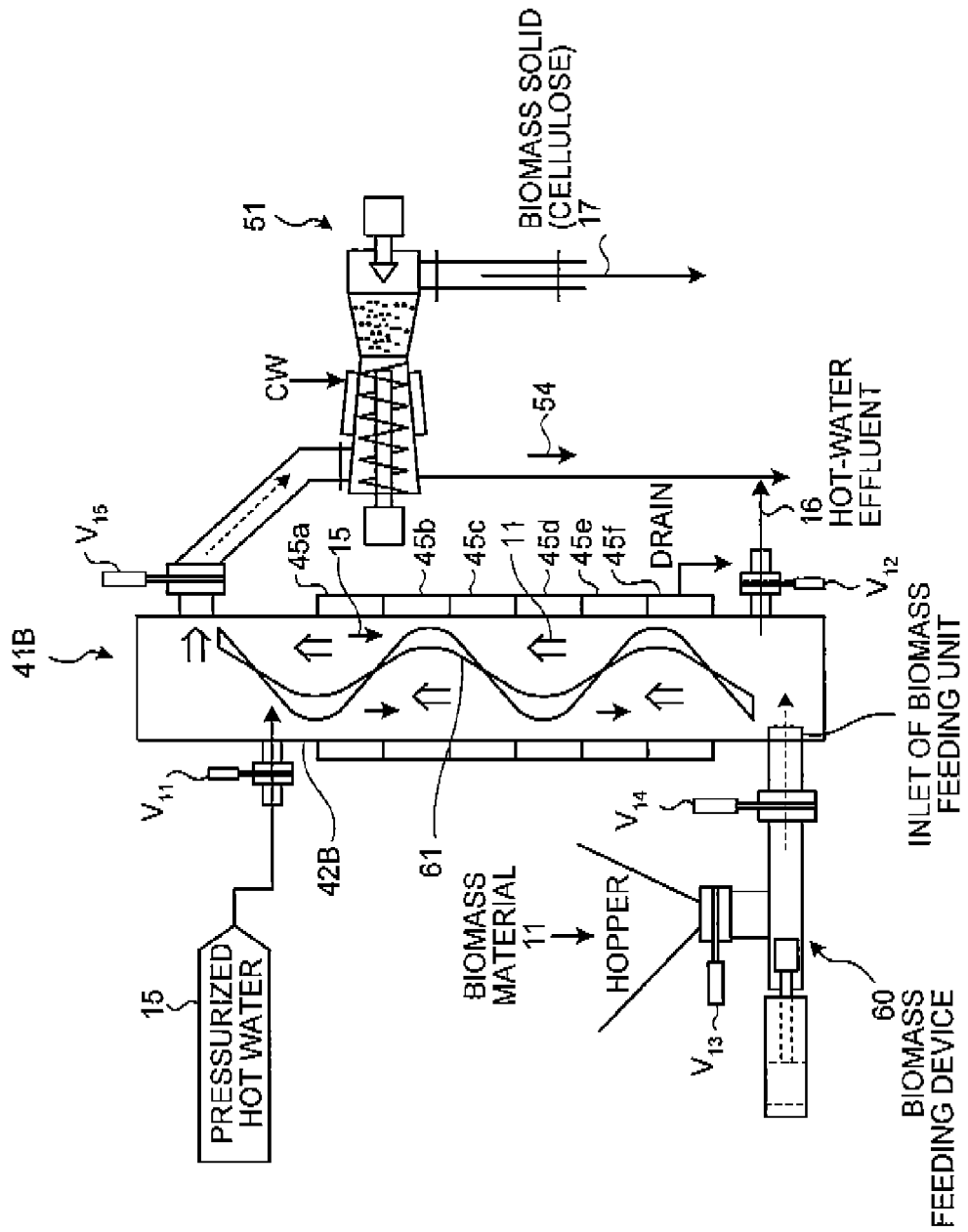
FIG. 8 is a schematic diagram of another biomass hydrothermal decomposition apparatus according to a third embodiment of the present invention.

FIG. 8 is a schematic diagram of another biomass hydrothermal decomposition apparatus according to a third embodiment.

As shown in FIG. 8, a biomass hydrothermal decomposition apparatus 41B according to the present embodiment includes: a biomass feeding device 60 that feeds the biomass material 11 (for example, wheat straw) under a normal pressure to under an increased pressure; and the hydrothermal decomposition apparatus 41B that gradually moves the fed biomass material 11 from either end side of upper and lower ends (in the present embodiment, the lower end) in a vertical apparatus body (hereinafter, "apparatus body") 42B in a consolidated state, feeds the pressurized hot water 15 from an end (in the present embodiment, the upper end side) different from a feed position of the biomass material 11 into the apparatus body 42B, hydrothermally decomposes the biomass material 11 while bringing the biomass material 11 into counter contact with the pressurized hot water 15, and transfers a lignin component and a hemicellulose component into the pressurized hot water 15 to separate the lignin component and the hemicellulose component from the biomass material 11. The hydrothermal decomposition apparatus 41B also includes the biomass discharging device 51 that discharges the biomass solid 17 from the feed position side of the pressurized hot water 15 of the apparatus body 42B under an increased pressure to under a normal pressure. Reference signs $V_{11}$ to $V_{15}$ denote ON-OFF valves.

The biomass feeding device 60 that feeds the biomass under a normal pressure to under an increased pressure includes a pump unit such as a piston pump or a slurry pump.

In the present embodiment, inside the apparatus body 42B, there is provided a fixed stirring unit 61 that stirs the biomass material 11 in a consolidated state, in a so-called plug flow, so that the biomass material 11 to be fed therein is stirred by a stirring function, when moved axially.

By providing the fixed stirring unit 61, mixture of the pressurized hot water 15 on the surface of the solid and inside the solid is progressed in the apparatus body 42B to facilitate reaction.

In the present invention, as for the flow of the pressurized hot water 15 and the biomass material 11 in the apparatus body 42B of the hydrothermal decomposition apparatus 41B, it is desired that the biomass material 11 and the pressurized hot water 15 are stirred and caused to flow in a so-called counter flow in which the biomass material 11 and the pressurized hot water 15 are brought into counter contact with each other.

The hydrothermal decomposition apparatus 41B performs hydrothermal decomposition in a plug flow. Therefore, its configuration is simple, and the solid biomass material 11 moves parallel to a central axis of a pipe, while being stirred vertically to the central axis of the pipe. Meanwhile, the pressurized hot water 15 (hot water, liquid dissolving decomposed products) moves while being soaked between solid particles by a counter flow against the solid.

Further, in the plug flow, a uniform flow of the pressurized hot water 15 can be realized. It is because when the solid biomass material 11 is decomposed by the pressurized hot water 15, the decomposed product dissolves on the hot water side, and thus the viscosity around a decomposed portion increases, so that hot water moves preferentially to around an undecomposed portion, then causing decomposition of the undecomposed portion. This configuration creates a uniform flow of hot water, thereby realizing uniform decomposition.

In the apparatus body 42B, due to the resistance of an inner pipe wall of the apparatus body 42B in the hydrothermal decomposition apparatus 41B, the solid density on the outlet side of the biomass material 11 is reduced as compared with that on the inlet side of the biomass material 11. In addition, the amount of the biomass solid 17 decreases due to the decomposition, to increase the ratio of the pressurized hot water 15. Consequently, the liquid retention time increases, causing excessive decomposition of decomposed components in the liquid. Therefore, at least the fixed stirring unit 61 is provided.

At this time, a temperature jacket, which is a temperature adjusting apparatus of the apparatus body 41A, is divided into a plurality of the elements 45a to 45f constituted by the heating-medium feeding units 45a to 45d as an internal-temperature maintaining unit and the cooling-medium feeding units 45e to 45f as an internal-temperature cooling unit.

Temperature control for maintaining a predetermined temperature (for example, 200° C.) with the pressurized hot water 15 being fed is then performed, by a controller which is not shown, by feeding a heating medium at a predetermined temperature in the heating-medium feeding units 45a to 45d, thereby efficiently effecting hydrothermal decomposition.

Thereafter, temperature control is performed, by the controller, to drop the temperature quickly from the hydrothermal decomposition temperature (200° C.) to a temperature (140° C.) at which excessive decomposition does not proceed, by feeding a cooling medium at a predetermined temperature in the cooling-medium feeding units 45e to 45f, in order to suppress excessive decomposition of the hydrothermally solubilized hemicellulose, which has become solubilized fractions due to the cooling medium. Therefore, excessive decomposition of hemicellulose, which is a hydrothermally solubilized component, is suppressed. Accordingly, a decrease in the yield of C5 sugar is reduced.

In the present embodiment, a temperature jacket has been explained as an example of the temperature adjusting apparatus. However, the present invention is not limited thereto, and for example, a method of injecting cold water or a temperature adjusting method by external heat exchange can be appropriately used.

Fourth Embodiment

A production system of alcohol, which is an organic material, using a biomass material according to a fourth embodiment of the present invention is explained with reference to the drawings.

FIG. 9 is a conceptual diagram of a production system of an organic material using the biomass material according to the present embodiment.

As shown in FIG. 9, an alcohol production system 10A using the biomass material according to the present embodiment includes a pre-processing device 12 that performs, for example, milling of the biomass material 11, the hydrothermal decomposition apparatus 41A shown in FIG. 7 that performs hydrothermal decomposition of the biomass material, while bringing a preprocessed biomass milled product 13 into counter contact with the pressurized hot water 15, to transfer the lignin component and the hemicellulose component into the pressurized hot water 15, thereby separating the lignin component and the hemicellulose component from a biomass solid, a first enzymatic decomposition device 19-1 that processes cellulose in the biomass solid 17 discharged from the hydrothermal decomposition apparatus 41A with enzyme to decompose cellulose into a sugar solution containing hexose by a first enzyme (cellulase) 18-1, a first alcohol fermentor 21-1 that produces alcohol (ethanol in the present embodiment) by fermentative treatment by using a first sugar solution (hexose) 20-1 obtained by the first enzymatic decomposition device 19-1, and a first refinery 25-1 that refines a first alcohol fermentation liquor 22-1 to separate the first alcohol fermentation liquor 22-1 into ethanol 23, which is a desired product, and a residue 24-1.

According to the present invention, in the biomass hydrothermal decomposition apparatus 41A, 41B as shown in FIG. 7 and FIG. 8, the lignin component and the hemicellulose component are transferred into the pressurized hot water 15 on the liquid side by adopting counter flow, so that cellulose remains in the biomass solid 17 on the solid side, thereby acquiring the first sugar solution (hexose) 20-1 by the first enzymatic decomposition device 19-1 for enzymic saccharification.

Accordingly, a fermenting process according to hexose (fermentation according to an end product: in the present embodiment, the ethanol 23 is obtained due to fermentation by using the first alcohol fermentor 21-1) can be established.

In the present embodiment, ethanol of alcohol is exemplified as the product to be obtained by the fermentative treatment. However, the present invention is not limited thereto, and petroleum substitutes, which become chemical product raw materials, or amino acid, which becomes a food/feed material other than alcohol can be obtained by the fermentor.

Various materials such as LPG, automotive fuel, aircraft jet fuel, kerosene petroleum, diesel oil, various heavy oils, fuel gas, naphtha, ethylene glycol as naphtha decomposition product, ethanol amine, alcohol ethoxylate, vinyl chloride polymer, alkyl aluminum, PVA, vinyl acetate emulsion, polystyrene, polyethylene, polypropylene, polycarbonate, MMA resin, nylon, and polyester can be efficiently produced as a chemical product from a sugar solution. Therefore, the sugar solution derived from biomass can be efficiently used as substitutes of chemical products derived from crude oil, which is a depleting fuel, and as a raw material for producing the substitutes.

Fifth Embodiment

A production system of alcohol, which is an organic material, using a biomass material according to a fifth embodiment of the present invention is explained with reference to the drawings.

Figure 10:
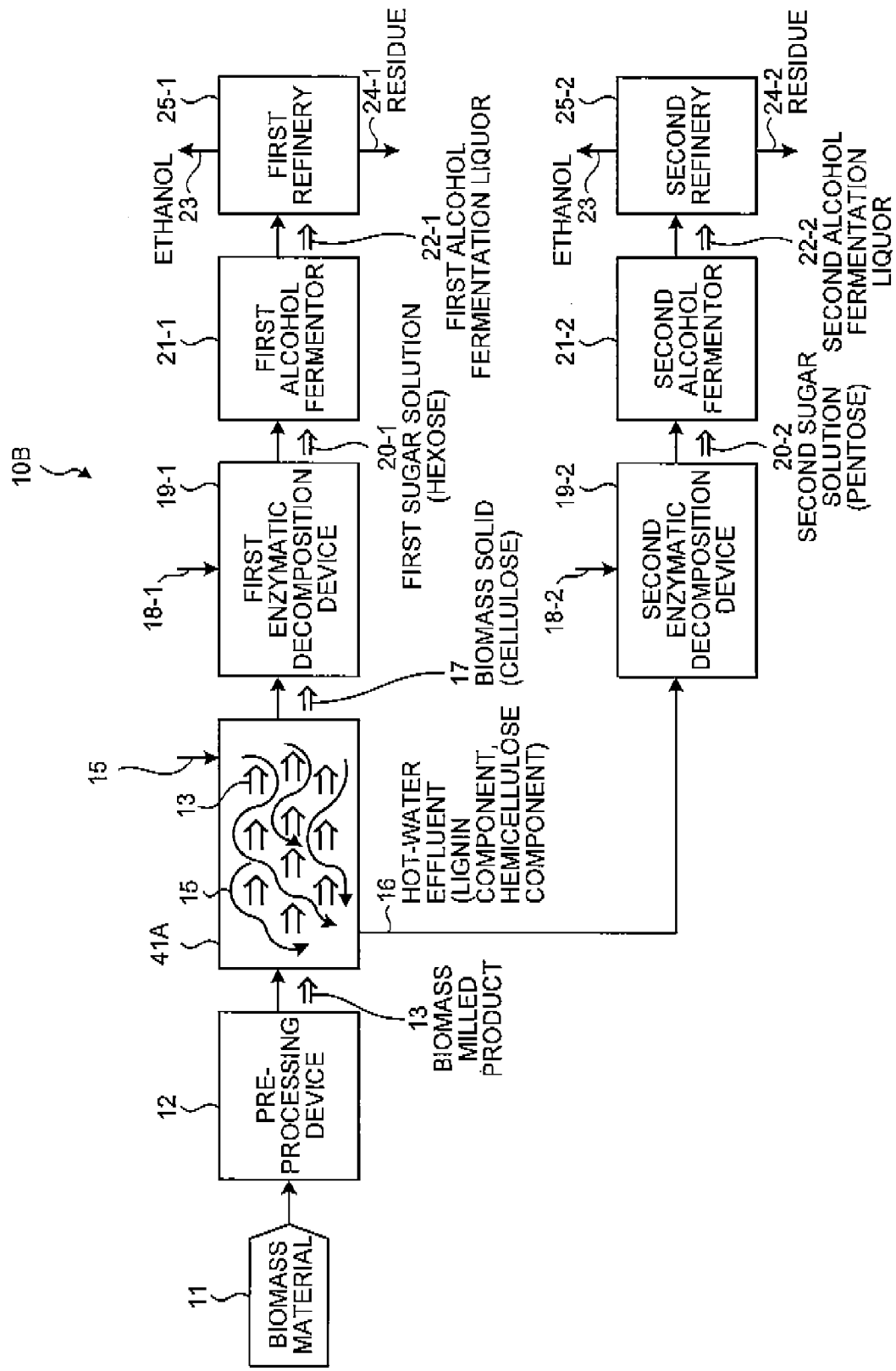
FIG. 10 is a schematic diagram of a production system of alcohol as an organic material using a biomass material according to a fifth embodiment of the present invention.

FIG. 10 is a conceptual diagram of a production system of alcohol, which is an organic material, using the biomass material according to the present embodiment.

As shown in FIG. 10, an alcohol production system 10B using the biomass material according to the present embodiment includes a second enzymatic decomposition device 19-2 that processes a hemicellulose component transferred into the hot-water effluent 16 discharged from the hydrothermal decomposition apparatus 41A with enzyme, to decompose the hemicellulose component into a second sugar solution 20-2 containing pentose, in the alcohol production system 10A shown in FIG. 9.

Two enzymatic decomposition devices, two alcohol fermentors, and two refineries (a first enzymatic decomposition device 19-1 and a second enzymatic decomposition device 19-2, a first alcohol fermentor 21-1 and a second alcohol fermentor 21-2, and a first refinery 25-1 and a second refinery 25-2) are provided separately. The ethanol 23 is obtained by performing an enzymatic decomposition process, an alcohol fermentation process, and a refining process according to the first sugar solution (hexose) 20-1 and the second sugar solution (pentose) 20-2.

In the present embodiment, after a second alcohol fermentation liquor 22-2 is obtained by the fermentation process performed by the second alcohol fermentor 21-2 by using the second sugar solution (pentose) 20-2 obtained by the second enzymatic decomposition device 19-2 using the second enzyme 18-2, the ethanol 23 can be produced by the second refinery 25-2. Reference numeral 24-2 denotes a residue.

Hot-water effluent is not always processed in separate systems, and various changes can be made such that, for example, a process after the enzymatic decomposition device is communalized, a process after the alcohol fermentor is communalized, or a process after the refinery is communalized.

Figure 11:
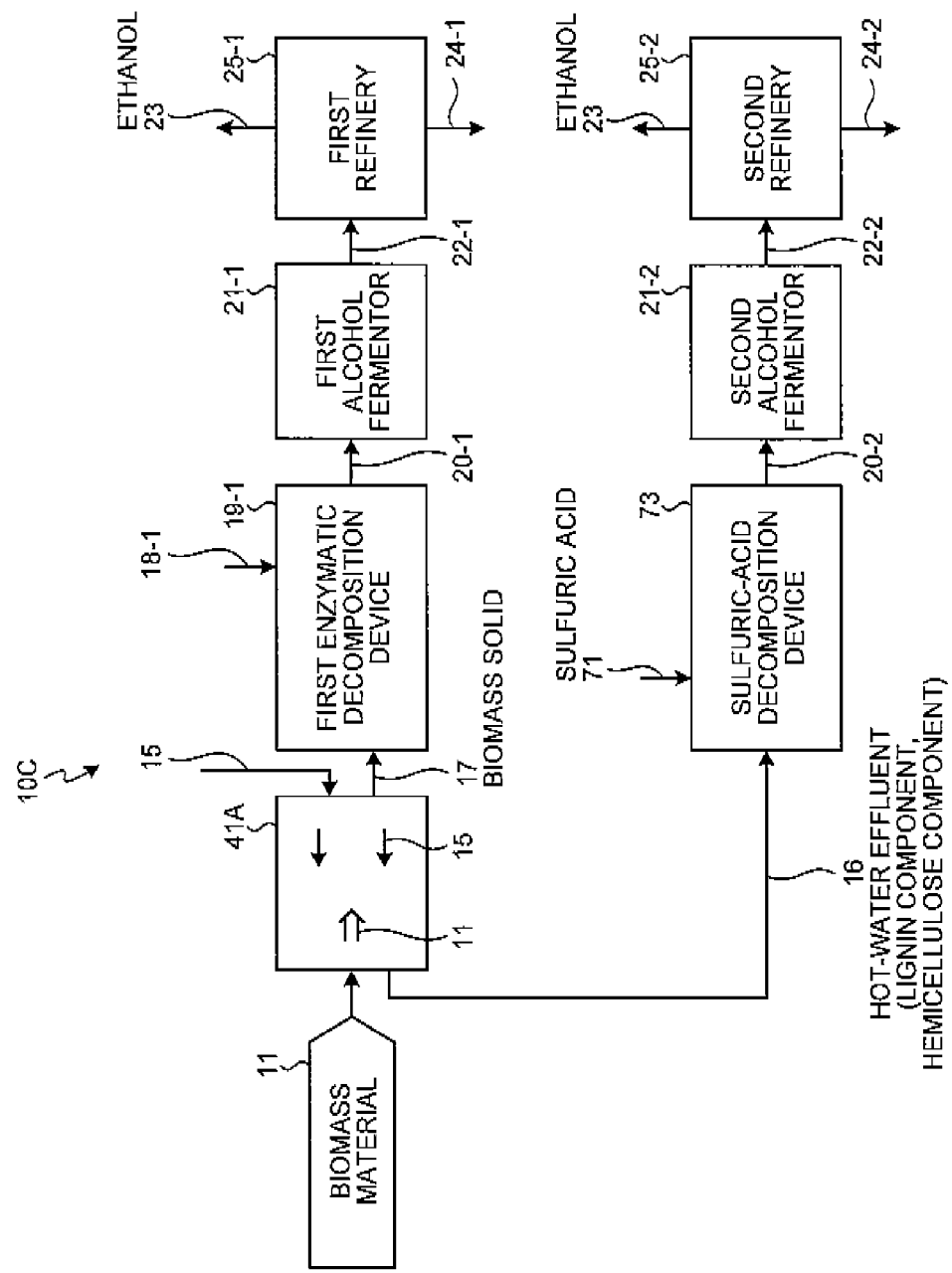
FIG. 11 is a schematic diagram of another production system of alcohol as an organic material using a biomass material according to the fifth embodiment.

FIG. 11 is a conceptual diagram of a production system of alcohol, which is an organic material using a biomass material according to a modification of the present embodiment.

As shown in FIG. 11, in the alcohol production system 10A shown in FIG. 9, an alcohol production system 10C according to the present embodiment includes a sulfuric-acid decomposition device 73 that discharges the pressurized hot water 15, into which the lignin component and the hemicellulose component are transferred, to outside as the hot-water effluent 16, feeds sulfuric acid 71 to the hot-water effluent 16, and decomposes the hemicellulose component in the hot-water effluent 16 with sulfuric acid to decompose the hemicellulose component into the second sugar solution 20-2 containing pentose, the second alcohol fermentor 21-2 that produces alcohol (ethanol in the present embodiment) by the fermentative treatment by using the obtained second sugar solution (pentose) 20-2, and the second refinery 25-2 that refines the second alcohol fermentation liquor 22-2 to separate the second alcohol fermentation liquor 22-2 into the ethanol 23, which is a desired product, and a second residue 24-2.

In the present embodiment, the ethanol 23 can be produced by the fermentative treatment by using the second sugar solution (pentose) 20-2 obtained by the sulfuric-acid decomposition device 73.

Decomposition conditions for the sulfuric-acid decomposition device in the present invention are such that concentration of sulfuric acid is 0.1% to 5% by weight, preferably, 1% to 4% by weight, decomposition temperature is 100° C. to 140° C., preferably about 120° C., and a decomposition time is for 30 minutes to 3 hours, preferably, about 1 hour. This is because, if the decomposition conditions are outside these ranges, favorable decomposition of hemicellulose cannot be realized.

Conventionally, when the biomass material is directly decomposed with sulfuric acid, the decomposition process is performed at a temperature as high as about 180° C. for about 10 minutes, by using 1% by weight of sulfuric acid. However, because sulfuric acid acts as an inhibitor at the time of enzymic saccharification of cellulose on a downstream side, the yield of hexose decreases.

On the other hand, in the present invention, in the biomass hydrothermal decomposition apparatus 41A, the cellulose component is caused to remain in the biomass solid 17 beforehand, to process the hot-water effluent 16 containing the hemicellulose component transferred to the pressurized hot water 13 side with sulfuric acid under a low-temperature condition. Therefore, the structure of sulfuric acid facilities can be simplified, and a usage amount of sulfuric acid can be considerably suppressed (to 0.6 to 0.9 times the conventional usage amount of sulfuric acid). As a result, the amount of disposal (gypsum treatment) of sulfuric acid is reduced, thereby enabling to reduce the facility size for recovering and separating sulfuric acid and downsize the facilities.

Because decomposition using sulfuric acid can be performed at a temperature as low as 140° C. or lower, any conventional heat-resistant facilities for high temperature (180° C.) is not required, thereby enabling to reduce the cost of the facilities.

According to the present invention, in the biomass hydrothermal decomposition apparatus 41A (41B), by adopting counter flow, cellulose remains in the biomass solid 17 on the solid side, and the first enzymatic decomposition device 19-1 for enzymic saccharification obtains the first sugar solution (hexose) 20-1, and in the pressurized hot water 15 on the liquid side, the hemicellulose component dissolved in the pressurized hot water 15 is separated as the hot-water effluent 16. The second enzymatic decomposition device 19-2 for enzymic saccharification or the sulfuric-acid decomposition device 73 obtains the second sugar solution (pentose) 20-2 separately. Therefore, the both sugar solutions can be efficiently separated and saccharized, respectively. The fermentation process according to hexose and pentose (fermentation according to the end product: for example, ethanol fermentation) can be established.

As described above, by adopting counter flow in the biomass hydrothermal decomposition apparatus 41A (41B), a side reaction product, which becomes an inhibitor in the enzymic saccharification reaction for obtaining hexose, and the lignin component soluble in pressurized hot water are transferred to the pressurized hot water 15 side. Therefore, the cellulose-based biomass solid 17 can be obtained, thereby improving the saccharification yield of hexose in the saccharification reaction thereafter.

On the other hand, the hemicellulose component contained in the separated hot-water effluent 16 is saccharized in the second enzymatic decomposition device 19-2, thereby enabling to obtain the sugar solution containing pentose.

By using a fermentum or the like suitable for hexose and pentose, respectively, the ethanol 23 can be efficiently and individually obtained by fermentation.

Further, at the time of the hydrothermal reaction, in the reaction apparatus, there are provided the effective reaction region (the hydrothermal decomposition region) A formed from the other side to the one side of the apparatus body 42, in which the feeding temperature of the pressurized hot water 15 (180 to 240° C., such as 200° C.) is maintained for a certain period of time to cause hydrothermal decomposition, and the temperature drop region (the dissolved-hemicellulose excessive decomposition suppressing region) B in which the temperature is rapidly dropped (for example, from 200° C. to 140° C.) to a temperature (for example, 140° C.) at which the hot-water soluble fractions are not excessively decomposed, immediately after it is out of the effective reaction region A. As a result, excessive decomposition of hemicellulose is suppressed, and thus a decrease in the yield of C5 sugar can be suppressed.

As described above, according to the present invention, a production system of an organic material using a biomass material that separates cellulose-based component and hemicellulose component transferred to pressurized hot water, suppresses excessive decomposition of hemicellulose, to enable efficient production of the sugar solutions (a hexose solution and a pentose solution) suitable for respective components, and can efficiently produce various organic materials (for example, alcohol, petroleum substitutes, or amino acid) from the sugar solution can be provided.

INDUSTRIAL APPLICABILITY

As described above, the hydrothermal decomposition apparatus according to the present invention separates a component mainly including cellulose from a biomass material and efficiently produces a sugar solution. Further, various organic materials (for example, alcohol, petroleum substitutes, or amino acid) can be efficiently produced from the sugar solution.

REFERENCE SIGNS LIST

11 biomass material
12 pre-processing device
13 biomass milled product
15 pressurized hot water
16 hot-water effluent
17 biomass solid
18 enzyme
19-1 first enzymatic decomposition device
19-2 second enzymatic decomposition device
20-1 first sugar solution (hexose)
20-2 second sugar solution (pentose)
23 ethanol
41A, 41B hydrothermal decomposition apparatus
42 apparatus body
43 transfer screw
45a to 45f multistage jacket
100 controller
110 hot water
111 cold water

The invention claimed is:

1. A biomass hydrothermal decomposition apparatus comprising:
an apparatus body that brings a solid biomass material into counter contact with a pressurized hot water and hydrothermally decomposes the solid biomass material so as to dissolve hot-water soluble fractions of the solid biomass material into the hot water;
a biomass material inlet that supplies the solid biomass material into the apparatus body, the biomass material inlet being provided on one side of the apparatus body;
a pressurized hot water inlet that supplies the pressurized hot water into the apparatus body, the pressurized hot water inlet being provided on other side of the apparatus body;
a biomass solid outlet that discharges a biomass solid of the solid biomass material, the biomass solid outlet being provided on the other side of the apparatus body;
a hot-water effluent outlet that discharges the hot-water soluble fractions as a hot-water effluent, the hot-water effluent outlet being provided on the one side of the apparatus body;
a plurality of pairs of an internal-temperature maintaining unit and a first temperature measuring unit that are provided between the pressurized hot water inlet and the hot-water effluent outlet of the apparatus body to form an effective reaction region, each of the internal-temperature maintaining units of the plurality of pairs feeding a heating medium via a heating medium valve so as to maintain a temperature of the pressurized hot water, the internal temperature maintaining unit and the first temperature measuring unit of each of the pairs being provided at the same level with respect to a vertical direction of the apparatus body;
a plurality of pairs of an internal-temperature cooling unit and a second temperature measuring unit that are provided between the pressurized hot water inlet and the hot-water effluent outlet of the apparatus body to form a temperature drop region and a gradual cooling region, each of the internal-temperature cooling units of the plurality of pairs feeding a cooling medium via a cooling medium valve so as to rapidly drop a temperature of the pressurized hot water, the pairs of the internal temperature cooling unit and the second temperature measuring unit of each of the pairs being provided at the same level with respect to the vertical direction of the apparatus body; and
a controller that controls the heating medium valves and the cooling medium valves based on a series of temperature measurement results obtained by the first and second temperature measuring units to form the effective reaction region and the temperature drop region, wherein
the hydrothermal decomposition apparatus is a vertical apparatus,
in the effective reaction region, the solid biomass material is hydrothermally dissolved and a lignin component and a hemicellulose component are transferred from the solid biomass material into the pressurized hot water,
in the temperature drop region excessive decomposition of the hemicellulose component is suppressed, and
the effective reaction region, the temperature drop region and the gradual cooling region are sequentially formed in the apparatus body from the pressurized hot water inlet to the hot-water effluent outlet.

2. The biomass hydrothermal decomposition apparatus according to claim 1, further comprising;
   a first circulation line that is connected between the apparatus body and the series of internal-temperature cooling units and extracts a part of the hot water from the apparatus body;
   a first heat exchanger that is interposed on the first circulation line and cools the extracted hot water, the cooled water from the first heat exchanger being supplied to the series of internal-temperature cooling units as the cooling medium;
   a second circulation line that is connected between the apparatus body and the series of internal-temperature maintaining units and extracts a part of the hot water from the apparatus body; and
   a second heat exchanger that is interposed on the second circulation line and adjusts the extracted hot water from the second circulation line, the adjusted water from the second heat exchanger being supplied to the series of internal temperature maintaining units as the heating medium.

3. The biomass hydrothermal decomposition apparatus according to claim 1, wherein
   a temperature of the pressurized hot water in the effective reaction region is greater than or equal to 180° C. and smaller than or equal to 240° C., and
   a temperature of the pressurized hot water in the temperature drop region is greater than or equal to 140° C. and smaller than 180° C.

4. An organic raw material production system using a biomass material, the system comprising:
   a pre-processing apparatus that pre-processes a solid biomass material including cellulose and hemicellulose;
   the biomass hydrothermal decomposition apparatus according to claim 1;
   a first enzymatic decomposition device that processes, with an enzyme, cellulose in the biomass solid discharged from the biomass hydrothermal decomposition apparatus to decompose cellulose into a sugar solution containing hexose with the enzyme; and
   a fermentation device that produces any one of alcohol, substitutes for petroleum, and amino acid by fermentative treatment, by using a sugar solution obtained by the first enzymatic decomposition device.

5. The organic raw material production system using a biomass material according to claim 4, the system comprising:
   a second enzymatic decomposition device that processes, with an enzyme, hemicellulose in the hot-water effluent to decompose hemicellulose into a sugar solution containing pentose with the enzyme; and
   a fermentation device that produces any one of alcohol, substitutes for petroleum, and amino acid by fermentative treatment, by using a second sugar solution obtained by the second enzymatic decomposition device.

6. The organic raw material production system using a biomass material according to claim 4, the system comprising:
   a sulfuric-acid decomposition device that decomposes, with sulfuric acid, a hemicellulose component in the hot-water effluent discharged from the hydrothermal decomposition apparatus to decompose the hemicellulose component into a second sugar solution containing pentose; and
   a second fermentation device that produces any one of alcohol, substitutes for petroleum, and amino acid by fermentative treatment, by using a second sugar solution obtained by the sulfuric-acid decomposition device.

7. The biomass hydrothermal decomposition apparatus of claim 1, wherein the plurality of pairs of the internal-temperature maintaining unit and the first temperature unit further comprise a heating medium inlet feeding the heating medium through the heating medium valve, and the plurality of pairs of the internal-temperature cooling unit and the second temperature measuring unit further comprise a cooling medium inlet feeding the cooling medium via the cooling medium valve.

* * * * *